US010041070B2

United States Patent
Berriel Diaz et al.

(10) Patent No.: US 10,041,070 B2
(45) Date of Patent: Aug. 7, 2018

(54) MICRORNAS MODULATING THE EFFECT OF GLUCOCORTICOID SIGNALING

(71) Applicants: Deutsches Krebsforschungszentrum Stiftung des Öffentlichen Rechts, Heidelberg (DE); Ruprecht-Karls-Universität Heidelberg, Heidelberg (DE)

(72) Inventors: Mauricio Berriel Diaz, München (DE); Roldan De Guia, Copenhagen (DK); Stephan Herzig, Baldham (DE)

(73) Assignees: Deutsches Krebsforschungszentrum Stiftung des Öffentlichen Rechts, Heidelberg (DE); Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 15/033,442

(22) PCT Filed: Oct. 28, 2014

(86) PCT No.: PCT/EP2014/073115
§ 371 (c)(1),
(2) Date: Apr. 29, 2016

(87) PCT Pub. No.: WO2015/063081
PCT Pub. Date: May 7, 2015

(65) Prior Publication Data
US 2016/0251656 A1    Sep. 1, 2016

(30) Foreign Application Priority Data
Oct. 29, 2013   (EP) .................................... 13190740

(51) Int. Cl.
*C12N 15/113*    (2010.01)
(52) U.S. Cl.
CPC ........ *C12N 15/113* (2013.01); *C12N 15/1136* (2013.01); *C12N 2310/11* (2013.01); *C12N 2310/113* (2013.01); *C12N 2310/141* (2013.01); *C12N 2310/315* (2013.01); *C12N 2310/3231* (2013.01); *C12N 2320/30* (2013.01)
(58) Field of Classification Search
None
See application file for complete search history.

(56) References Cited

FOREIGN PATENT DOCUMENTS

| WO | WO 2005/099770 A2 | 10/2005 |
|---|---|---|
| WO | WO 2012/145374 A1 | 10/2012 |
| WO | WO 2013/159091 A2 | 10/2013 |

OTHER PUBLICATIONS

Bernecker, C. et al., "MicroRNA Expressions in PMBCs, CD4+, and CD8+ T-Cells from Patients Suffering from Autoimmune Addison's Disease," *Horm Metab Res*, 2013, 45:599-604.
Carrer, Michele et A, "Control of mitochondrial metabolism and systemic energy homeostasis by microRNAs 378 and 378," *PNAS*, Sep. 18, 2012, 109(38):15330-15335.
Chartoumpekis, Dionysios V. et al., "Differential Expression of MicroRNAs in Adipose Tissue after Long-Term High-Fat Diet-Induced Obesity in Mice," *PLoS One*, Apr. 2012, 7(4):1-13.
De Guia, Roldan M. et al., "MicroRNA-379 couples glucocorticoid hormones to dysfunctional lipid homeostasis," *The EMBO Journal*, 2015, 34(3):344-361.
Dehwah, Mustafa Abdo Saif et al., "MicroRNAs and Type 2 Diabetes/Obesity," *Journal of Genetics and Genomics*, 2012, 39:11-18.
Hennessy, Erica et al., "Identification of microRNAs with a role in glucose stimulated insulin secretion by expression profiling of MIN6 cells," *Biochemical and Biophysical Research Communications*, 2010, 396:457-462.
Hilton, C. et al., "MicroRNAs in adipose tissue: their role in adipogenesis and obesity," *International Journal of Obesity*, 2013, 37:325-332.
Rome, Sophie. "Are extracellular microRNAs involved in type 2 diabetes and related pathologies?" *Clinical Biochemistry*, 2013, 46:937-945.
Williams, Michael D. et al., "MicroRNAs in Insulin Resistance and Obesity," *Experimental Diabetes Research*, 2012, pp. 1-8.

*Primary Examiner* — Tracy Vivlemore
(74) *Attorney, Agent, or Firm* — Saliwanchik, Lloyd & Eisenschenk

(57) ABSTRACT

The present invention discloses microRNAs (miR) involved in the regulation of the lipid and glucose metabolism. Several conserved miR molecules were found as direct targets of the glucocorticoid hormone/glucocorticoid receptor signaling axis. Hence, the present invention pertains to inhibitors of these miRs—such as antimiRs and block-miRs—as well as isolated miR molecules or miR expression constructs for the treatment or prevention of metabolic disorders caused by deregulated glucocorticoid signaling, such as insulin resistance, the metabolic syndrome, obesity and/or diabetes type II. Particular preferred embodiments of the invention pertain to antagonists or agonists of a miR of the conserved miR-379-410 cluster, particularly of miR-379.

9 Claims, 21 Drawing Sheets

FIG. 3B
FIG. 3C
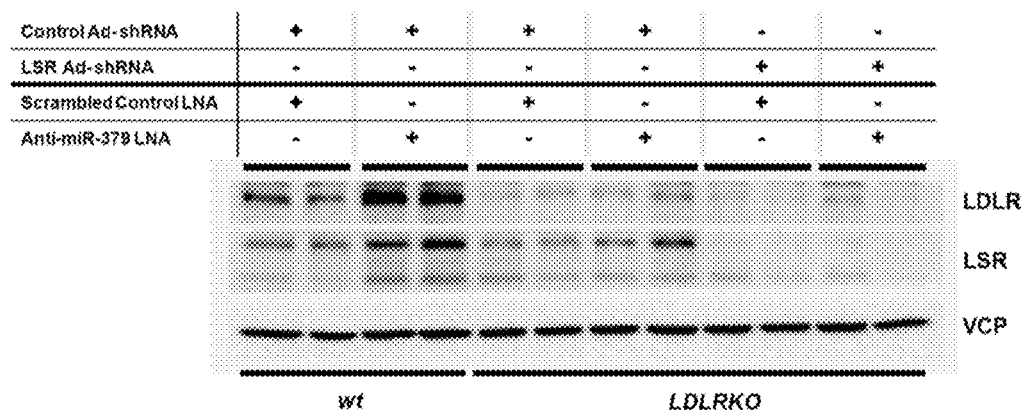
FIG. 3D
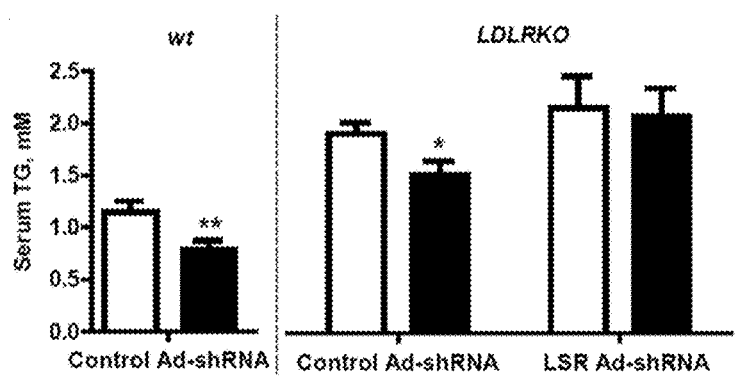
FIG. 3E

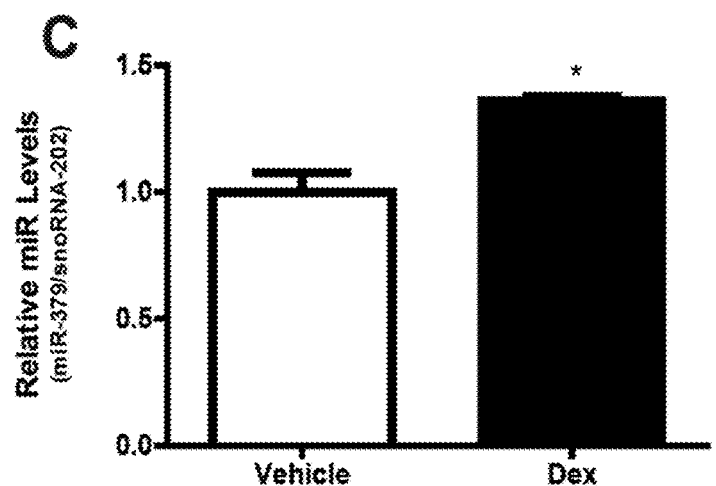
FIG. 5C
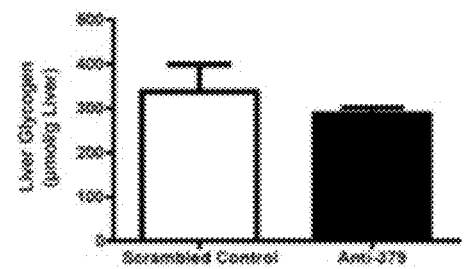
FIG. 6A
FIG. 6B
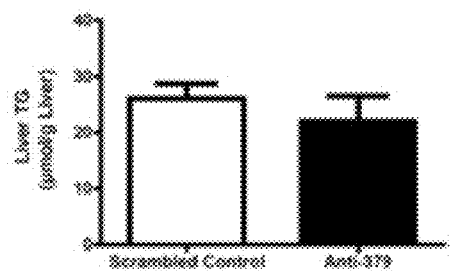
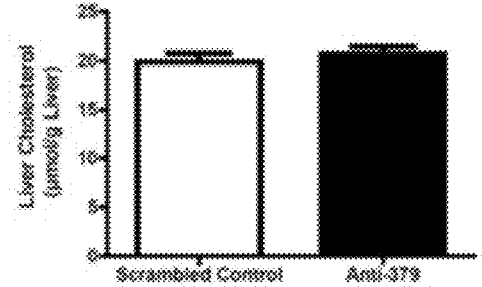
FIG. 6C
FIG. 6D

SEQUENCE LISTING

<160> NUMBER OF SEQ ID NOS: 14

<210> SEQ ID NO 1
<211> LENGTH: 21
<212> TYPE: DNA
<213> ORGANISM: Mus musculus

<400> SEQUENCE: 1
ugguagacua uggaacguag g          21

<210> SEQ ID NO 2
<211> LENGTH: 21
<212> TYPE: DNA
<213> ORGANISM: Homo sapiens

<400> SEQUENCE: 2
ugguagacua uggaacguag g          21

<210> SEQ ID NO 3
<211> LENGTH: 25
<212> TYPE: DNA
<213> ORGANISM: Mus musculus

<400> SEQUENCE: 3
aagggauucu gauguugguc acacu          25

<210> SEQ ID NO 4
<211> LENGTH: 25
<212> TYPE: DNA
<213> ORGANISM: Homo sapiens

<400> SEQUENCE: 4
aaaggauucu gcugucgguc ccacu          25

<210> SEQ ID NO 5
<211> LENGTH: 22
<212> TYPE: DNA
<213> ORGANISM: Mus musculus

<400> SEQUENCE: 5
ucggauccgu cugagcuugg cu          22

<210> SEQ ID NO 6
<211> LENGTH: 22
<212> TYPE: DNA
<213> ORGANISM: Homo sapiens

<400> SEQUENCE: 6
ucggauccgu cugagcuugg cu          22

<210> SEQ ID NO 7
<211> LENGTH: 22
<212> TYPE: DNA
<213> ORGANISM: Mus musculus

<400> SEQUENCE: 7
ugugacuggu ugaccagagg gg          22

<210> SEQ ID NO 8
<211> LENGTH: 22
<212> TYPE: DNA
<213> ORGANISM: Homo sapiens

<400> SEQUENCE: 8

```
ugugacuggu ugaccagagg gg                                              22

<210> SEQ ID NO 9
<211> LENGTH: 21
<212> TYPE: DNA
<213> ORGANISM: Mus musculus

<400> SEQUENCE: 9
gaacggcguc augcaggagu u                                               21

<210> SEQ ID NO 10
<211> LENGTH: 21
<212> TYPE: DNA
<213> ORGANISM: Homo sapiens

<400> SEQUENCE: 10
gaacggcuuc auacaggagu u                                               21

<210> SEQ ID NO 11
<211> LENGTH: 22
<212> TYPE: DNA
<213> ORGANISM: Mus musculus

<400> SEQUENCE: 11
gaaguuguuc gugguggauu cg                                              22

<210> SEQ ID NO 12
<211> LENGTH: 22
<212> TYPE: DNA
<213> ORGANISM: Homo sapiens

<400> SEQUENCE: 12
gaaguuguuc gugguggauu cg                                              22

<210> SEQ ID NO 13
<211> LENGTH: 15
<212> TYPE: DNA
<213> ORGANISM: Artificial
<220> FEATURE:
<223> OTHER INFORMATION: Antisense Molecule

<400> SEQUENCE: 13
gttccatagt ctacc                                                      15

<210> SEQ ID NO 14
<211> LENGTH: 15
<212> TYPE: DNA
<213> ORGANISM: Artificial
<220> FEATURE:
<223> OTHER INFORMATION: Scrambled Control

<400> SEQUENCE: 14
acgtctatac gccca                                                      15
```

MICRORNAS MODULATING THE EFFECT OF GLUCOCORTICOID SIGNALING

CROSS REFERENCE TO RELATED APPLICATIONS

This application is a National Stage Application of International Application Number PCT/EP2014/073115, filed Oct. 28, 2014; which claims priority to European Patent Application No. 13190740.4, filed Oct. 29, 2013; all of which are incorporated herein by reference in their entirety.

The Sequence Listing for this application is labeled "SeqList-21Apr16-ST25.txt", which was created on Apr. 21, 2016, and is 3 KB. The entire content is incorporated herein by reference in its entirety.

FIELD OF THE INVENTION

The present invention discloses microRNAs (miR) involved in the regulation of the lipid and glucose metabolism. Several conserved miR molecules were found as direct targets of the glucocorticoid hormone/glucocorticoid receptor signaling axis. Hence, the present invention pertains to inhibitors of these miRs—such as antimiRs and blockmiRs—as well as isolated miR molecules or miR expression constructs for the treatment or prevention of metabolic disorders caused by deregulated glucocorticoid signaling, such as insulin resistance, the metabolic syndrome, obesity and/or diabetes type II. Particular preferred embodiments of the invention pertain to antagonists or agonists of a miR of the conserved miR-379-410 cluster, particularly of miR-379.

DESCRIPTION

The metabolic syndrome (a constellation of metabolic disorders that all result from, or are associated with, a primary disorder of insulin resistance) is characterized by a group of metabolic risk factors including abdominal obesity, elevated triglyceride levels, decreased high-density lipoprotein (HDL) cholesterol levels, high blood pressure, and impaired fasting blood glucose, (a measure for decreased insulin sensitivity and increased risk of developing diabetes). Patients suffering from the metabolic syndrome are at increased risk of coronary heart disease and other atherosclerotic conditions such as stroke and peripheral vascular disease and diabetes type 2. The number of patients suffering from the metabolic syndrome particularly increased recently in developed countries like the United States and Europe.

The pathogenesis of the metabolic syndrome is multifactorial and polygenic; a long list of lifestyle and genetic parameters has been attributed to ultimately lead to the metabolic disorders described above. These include a sedentary lifestyle, lack of physical exercise, excess intake of dietary fat and its composition as well as several genes affecting glucose and lipoprotein metabolism. Several heritability studies indicated a major role for genetic susceptibility to the metabolic syndrome although the associations were quite weak and the replication of findings has been poor. In addition, recent data indicate a modulating effect of gene-nutrient interactions on the risk of onset for the metabolic syndrome and therapeutic dietary interventions.

The hypothalamic-pituitary-adrenal (HPA) endocrine axis is a critical physiological stress circuit to maintain body homeostasis during diverse situations such as trauma, exercise or nutrient deprivation (Rose et al., 2010). In metabolic control, GC signaling acts as a major counter-regulatory system against insulin action, and aberrantly elevated GC activity is tightly linked to major components of the Metabolic Syndrome, including obesity, insulin resistance, hyperglycemia, and systemic dyslipidemia. Indeed, GC levels have been found to be elevated in insulin-resistant patients and are strongly associated with a hyperglycaemic and fatty liver phenotype, mediated through the glucocorticoid receptor (GR), a member of the nuclear receptor transcription factor family (Opherk et al., 2004) (Lemke et al., 2008). In congruence, obesity is characterized by enhanced local GC action (Reynolds et al., 2001, and states of either endogenous or exogenous GC deficiency or excess, e.g. Addison's disease, Cushing's syndrome, or GC therapy, respectively, are characterized by severe perturbations in systemic energy metabolism that closely mimic aspects of the Metabolic Syndrome (Rose, 2013).

Recently, a class of small non-coding RNAs (microRNAs) has emerged as a critical but as-yet largely unexplored layer of metabolic control. MicroRNAs (miRNAs) are a class of small (e.g., 18-24 nucleotides) non-coding RNAs that exist in a variety of organisms, including mammals, and are conserved in evolution. miRNAs are processed from hairpin precursors of about 70 nucleotides which are derived from primary transcripts through sequential cleavage by the RNAse III enzymes drosha and dicer. Many microRNAs can be encoded in intergenic regions, hosted within introns of pre-mRNAs or within non-coding RNA genes. Many miRNAs also tend to be clustered and transcribed as polycistrons and often have similar spatial temporal expression patterns. MiRs have been found to have roles in a variety of biological processes including developmental timing, differentiation, apoptosis, cell proliferation, organ development, and metabolism. Indeed, individual miRNA have been found to regulate diverse aspects of energy homeostasis, including pancreatic beta cell insulin secretion, adipose tissue lipid storage, and hepatic cholesterol and lipid handling (Rottiers and Naar, 2012). However, no miRNA targets of the GC/GR axis in metabolic control have been identified to date.

In view of the above described background art, the objective of the present invention is to provide novel means to treat or prevent metabolic disorders associated with the glucocorticoid signaling axis.

The above problem was solved by the inventors who developed a set of target miRs which are directly involved in glucocorticoid (GC) signaling. The inventors provide herein both significantly upregulated and downregulated miRs in response to glucocorticoid receptor deficiency in a mouse model. The inventors identified the hepatic induction of the conserved micro (mi) RNA 379-410 cluster as a key molecular component of GC-driven metabolic dysfunction in obesity and diabetes ("diabesity"). Hepatocyte-specific silencing of miRNA379 led to a significant reduction of circulating very-low-density lipoprotein (VLDL)-associated triglyceride (TG) levels in wild-type mice, while miRNA379 overexpression in turn triggered hypertriglyceridemia in healthy animals. miRNA379 effects were mediated through the post-transcriptional silencing of key receptors in hepatic TG re-uptake. As hepatic deficiency in miRNA379 abrogated hypertriglyceridemia in diabetic preferably the miRNA379-410 cluster represents an attractive therapeutic target in GC-dependent pathologies, including diabesity-related dyslipidemia.

The invention provides two sets of miR which are both herein indicated for the use in medicine. Impairing the function and/or expression of a miR which is herein identified to be down-regulated in a glucocorticoid deficient background is thus indicated to be useful in the treatment of a disorder associated with increased activity of the glucocorticoid signaling axis (glucocorticoid excess). On the other hand, increasing the function and/or the expression of these miRs is indicated to be beneficial in a medical scenario characterized by an impaired glucocorticoid signaling (glucocorticoid deficit). The miRs comprised in this first set are miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-54, as well as the miRs of the miR-379-410 cluster (see below).

The second set of miR as identified in context of the present invention comprises miRs which are up-regulated in a glucocorticoid deficient background. Impairing the function and/or expression of such a miR which is herein identified to be up-regulated in a glucocorticoid deficient background is thus indicated to be useful in the treatment of a disorder characterized by an impaired glucocorticoid signaling. On the other hand, increasing the function and/or the expression of these miRs is indicated to be beneficial in a medical scenario associated with increased activity of the glucocorticoid signaling axis. The miRs comprised in this second set are miR-719, miR-483, miR-669j, miR-146a, miR-1948, miR-342-3p, miR-24-2*, miR-132, miR-182, mir-677 and miR-18a.

Thus, in a first aspect of the present invention, the above objective is solved by providing an inhibitor of a micro RNA (miR), or of a target site of a miR—preferably an antimiR or blockmiR, wherein the miR is selected from the group consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-541, for use in the treatment or prevention of a disease. These miRs were identified to be significantly down-regulated in response to glucocorticoid receptor deficiency (FIG. 1A).

"MicroRNA" means a non-coding RNA between 18 and 25 nucleobases in length, which is the product of cleavage of a pre-miRNA by the enzyme Dicer. Examples of mature miRNAs are found in the miRNA database known as miRBase (see Worldwide Website: microma.sanger.ac.uk/). In certain embodiments, microRNA is abbreviated as "miRNA" or "miR". In the context of the present invention the miR provided refer to mammalian, such as mouse, specifically human miRs.

"Pre-miRNA" or "pre-miR" means a non-coding RNA having a hairpin structure, which is the product of cleavage of a pri-miR by the double-stranded RNA-specific ribonuclease known as Drosha.

The term "inhibitor of a miR" shall be understood to refer to any compound suitable to impair the function and/or expression of a given miR. In preferred embodiments of the invention the term "inhibitor of a miR" shall refer to nucleic acid molecules or oligonucleotide compounds inhibiting the function and/or the expression of any of the miR of the present invention. Such nucleic acid molecules or oligonucleotide compounds are preferably characterized by comprising a sequence which is complementary to the sequence of a miR of the present invention—so called antisense molecules. Antisense molecules preferably comprise a sequence complementary to a sequence according to any one of SEQ ID NO: 1 to 12. Most preferably such an antisense molecule has the sequence of SEQ ID NO: 13.

The term "isolated miR molecule" refers to a nucleic acid molecule that comprises a sequence identical to—at least to a sufficient degree—a miR of the invention. The isolated miR molecule mimics the biological function of the respective miR.

The term "antimiR" means an oligonucleotide having a nucleobase sequence complementary to a microRNA. In certain embodiments, an antimiR is a modified oligonucleotide. The term "blockmiR" means an oligonucleotide binding to and blocking the target site of the miR on the respective target mRNA.

Inhibitors of a miR in the context of this invention are preferably inhibitory nucleic acids targeting the miR of the invention. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. The antisense sequence may be a blockmiR antisense sequence capable of binding to a microRNA binding site in a target RNA.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In preferred embodiments of the invention said disease to be treated and/or prevented with the use of the molecules of the invention is a pathology dependent on glucocorticoid signaling, such as glucocorticoid hormone driven metabolic dysfunction, and/or a disease associated with elevated serum levels of triglycerides, preferably the disease is selected from obesity, diabetes, diabesity, metabolic syndrome, insulin resistance, hyperglycemia, systemic dyslipidemia, Cushing's syndrome, adverse or side effects associated with or caused by glucocorticoid treatment or excess, atherosclerosis, heart disease, stroke and growth defects.

"Metabolic dysfunction" means a condition characterized by an alteration or disturbance in one or more metabolic processes in the body. Metabolic disorders include, but are not limited to, hyperglycemia, prediabetes, diabetes, type 1 diabetes, type 2 diabetes, obesity, diabetic dyslipidemia, metabolic syndrome, insulin resistance, and hyperinsulinemia. "Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Insulin resistance" means a condition in which normal amounts of insulin are inadequate to produce a normal insulin response from fat, muscle and liver cells. Insulin resistance in fat cells results in hydrolysis of stored triglycerides, which elevates free fatty acids in the blood. Insulin resistance in muscle reduces the uptake of glucose from the blood by muscle cells. Insulin resistance in liver reduces glucose storage and a failure to suppress glucose production. Elevated free fatty acids, reduced glucose uptake, and elevated glucose production all contribute to elevated blood glucose levels. High plasma levels of insulin and glucose due to insulin resistance often leads to metabolic syndrome and type 2 diabetes.

"Type 1 diabetes" means diabetes characterized by loss of the insulin-producing beta cells of the islets of Langerhans in the pancreas leading to a deficiency of insulin (also known as insulin-dependent diabetes mellitus or IDDM). Type I diabetes can affect children or adults, but typically appears between the ages of 10 and 16.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Diabetic dyslipidemia" or "Type 2 diabetes with dyslipidemia" means a condition characterized by Type 2 diabetes, reduced HDL-C, elevated serum triglycerides, and elevated small, dense LDL particles.

"Metabolic syndrome" means a condition characterized by a clustering of lipid and nonlipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Side effects or adverse effects of glucocorticoid treatment or excess" in context of the present invention refers amongst others to hyperglycemia due to increased gluconeogenesis, insulin resistance, and impaired glucose tolerance, weight gain due to increased visceral and truncal fat deposition (central obesity) and appetite stimulation.

The term "glucocorticoid excess" refers to patients afflicted with a condition associated with chronic exposure to above-normal levels of glucocorticoids. As a result, these patients can be characterized as having high blood levels of glucocorticoids. Examples include excessive secretion of adrenocortical hormones such as cortisol in Cushing's disease, or chronic exposure to glucocorticoids such as dexamethasone or prednisone used as antiinflammatory agents in many clinical scenarios such as renal transplantations.

Preferred embodiments of the invention pertain to the above inhibitors of a miR selected from the group consisting of miR-379, miR-541, miR-127, miR-134, miR-337-5p, miR-382, miR-592, miR-711, miR-762 and mir-2861; preferably wherein said miR is a miR from the miR-379-410 cluster, most preferably miR-379.

TABLE 1 murine and human miR-Sequences

| MicroRNA | Sequence | miRBase Accession Number | SEQ ID NO: |
|---|---|---|---|
| mmu-miR-379-5p | UGGUAGACUAUGG AACGUAGG | MIMAT0000743 | 1 |
| hsa-miR-379-5p | UGGUAGACUAUGG AACGUAGG | MIMAT0000733 | 2 |
| mmu-miR-541-5p | AAGGGAUUCUGAU GUUGGUCACACU | MIMAT0003170 | 3 |
| hsa-miR-541-5p | AAAGGAUUCUGCU GUCGGUCCCACU | MIMAT0004919 | 4 |
| mmu-miR-127-3p | UCGGAUCCGUCUG AGCUUGGCU | MIMAT0000139 | 5 |
| hsa-miR-127-3p | UCGGAUCCGUCUG AGCUUGGCU | MIMAT0000446 | 6 |
| mmu-miR-134-5p | UGUGACUGGUUGA CCAGAGGGG | MIMAT0000146 | 7 |
| hsa-miR-134 | UGUGACUGGUUGA CCAGAGGGG | MIMAT0000447 | 8 |
| mmu-miR-337-5p | GAACGGCGUCAUG CAGGAGUU | MIMAT0004644 | 9 |
| hsa-miR-337-5p | GAACGGCUUCAUA CAGGAGUU | MIMAT0004695 | 10 |
| mmu-miR-382-5p | GAAGUUGUUCGUG GUGGAUUCG | MIMAT0000747 | 11 |
| hsa-miR-382 | GAAGUUGUUCGUG GUGGAUUCG | MIMAT0000737 | 12 |

Preferably the various aspect and embodiments of the present invention relate to a miR comprising a sequence according to any one of SEQ ID NO: 1 to 12, most preferably according to a sequence of SEQ ID NO: 2, as well as to analogs, derivatives or homologs thereof.

When referring to a sequence of a specific miR in context of the present invention, both human and mouse sequences of said miR shall be comprised. In some embodiments the human miR sequences are preferred. The person of skill in the art knows the homologous sequences of a given miR, specifically known are the corresponding human and mouse sequences, which are well conserved.

The term "miR-379-410 cluster" as used in the context of the present invention pertains to a group of miRs consisting of miR-134, miR-136, miR-154, miR-300-3p, miR-300-5p, miR-323, miR-329, miR-369-3p, miR-369-5p, miR-376a, miR-376a*, miR-376b-3p, miR-376b-5p, miR-376c, miR- 377, miR-379, miR-379*, miR-382, miR-382*, miR-409-5p, miR-410, miR-411, miR-434, miR-485, miR-487b, miR-494, miR-495, miR-539, miR-541, miR-543*, and miR-758. Thus, the above term may refer to any one of the aforementioned miR comprised in the miR-379-410 cluster.

Another aspect of the present invention pertains to an inhibitor of a micro RNA (miR), or of a target site of a miR, such as an antimiR or blockmiR targeting a miR, or a target site of a miR, wherein the miR is selected from the group consisting of miR-719, miR-483, miR-669j, miR-146a, miR-1948, miR-342-3p, miR-24-2*, miR-132, miR-182, mir-677 and miR-18a for use in the treatment of a disease. These miRs were identified to be significantly upregulated in response to glucocorticoid receptor deficiency (FIG. 1A). Thus, in preferred embodiments of the invention inhibitors of the aforementioned miR are for use in the treatment or prevention of Addison's disease, or in increasing triglyceride serum levels in a patient, in particular for use in increasing the weight of said patient.

Preferred embodiments of the invention further pertain to inhibitors of said miR, comprising a sequence complementary to, or hybridizing under stringent conditions to, the sequence of said miR, or said target site of said miR respectively.

The invention encompasses sequences which hybridize under stringent conditions with the nucleotide sequence of any of the herein mentioned miR. The term "hybridization under stringent conditions" is used herein as in Sambrook et al. (Molecular Cloning, A Laboratory Manual, Cold Spring Harbor Laboratory Press (1989), 1.101-1.04). A stringent hybridization according to the invention is preferably present when a positive hybridization signal is observed after washing for 1 hour with 1×SSC and 0.1% SDS at 50° C., preferably at 55° C., more preferably at 62° C. and most preferably at 68° C. and more preferably for 1 hour with 0.2×SSC and 0.1% SDS (sodium dodecyl sulfate) at 50° C., preferably at 55° C., more preferably at 62° C. and most preferably at 68° C.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' 0-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

Preferred is for some embodiments that the at least one chemical modification of the nucleic acid molecule or oligonucleotide (the antisense molecule such as an antimiR or blockmiR) is selected from the group of nucleic acid analogs consisting of phosphorothioate DNA (PS), 2'-O-methyl RNA (OMe), 2'-O-methoxy-ethyl RNA (MOE), peptide nucleic acid (PNA), N3'-P5' phosphoroamidate (NP), 2'-fluoro-arabino nucleic acid (FANA), locked nucleic acid (LNA), morpholino phosphoroamidate (MF), cyclohexene nucleic acid (CeNA), or tricycle-DNA (tc-DNA).

In one particularly preferred embodiment there is provided an inhibitory nucleic acid molecule, comprising a sequence according to SEQ ID NO: 13 (GTTCCATAGTC-TACC), preferably which is provided as PNA.

Other aspects of the present invention pertain to miR molecules, or means of increasing the expression or increasing the activity of said miR molecules. The miR molecules in accordance with the present invention are preferably isolated nucleic acid molecules having a sequence at least 80% or more identical to the sequences of the herein disclosed groups of miR.

Thus, in one further aspect the above problem is solved by a (isolated) miR molecule selected from the group consisting of miR-719, miR-483, miR-669j, miR-146a, miR-1948, miR-342-3p, miR-24-2*, miR-132, miR-182, mir-677 and miR-18a, for use in the treatment of prevention of a disease. These miRs were found to be upregulated in response to GC deficiency. Thus, preferred embodiments of the invention pertain to the use of these miR in the treatment or prevention of a disease which is dependent on glucocorticoid signaling, preferably glucocorticoid hormone driven metabolic dysfunction, and/or a disease associated with elevated serum levels of triglycerides; preferably the disease is selected from obesity, diabetes, such as diabetes II, diabesity, metabolic syndrome, insulin resistance, hyperglycemia, systemic dyslipidemia, Cushing's syndrome, adverse effects associated with glucocorticoid-treatment, atherosclerosis, heart disease, stroke and growth defects.

In this aspect it is particularly preferred to select the miR from the group consisting of miR-210, miR-221, miR-222, miR-34a and miR-18a.

Another aspect of the present invention then pertains to a (isolated) miR molecule selected from the group consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-541, for use in the treatment or prevention of a disease. These miRs were found to be significantly downregulated in response to glucocorticoid receptor deficiency. Thus in preferred embodiments said miRs are for use in the treatment or prevention of Addison's disease, or in increasing triglyceride serum levels in a patient, in particular for use in increasing the weight of said patient.

In this aspect of the invention preferred embodiments pertain to a miR is selected from the group consisting of miR-379, miR-541, miR-127, miR-134, miR-337-5p, miR-382, miR-592, miR-711, miR-762 and mir-2861; preferably wherein said miR is a miR from the miR-379-410 cluster, most preferably miR-379.

In certain embodiments, an oligonucleotide of the invention—meaning a nucleic acid inhibitor of any of the miR of the invention, or alternatively a miR molecule or an expression construct of a miR molecule of the invention—has a nucleobase sequence that is complementary to or identical to a nucleobase sequence having at least 80% identity to a nucleobase sequence of a miR selected from the group (downregulated in glucocorticoid receptor deficiency) consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 miR-541; or the group (upregulated in glucocorticoid receptor deficiency) consisting of miR-719, miR-483, miR-669j, miR-146a, miR-1948, miR-342-3p, miR-24-2*, miR-132, miR-182, mir-677 and miR-18a. In certain embodiments, an oligonucleotide has a nucleobase sequence that is complementary to or identical to a nucleobase sequence having at least 85%, at least 90%, at least 92%, at least 94%, at least 96%, at least 98% identity, or 100% identity to a nucleobase sequence of a miR as mentioned before. The most preferred miR of the invention for the above described embodiments is miR-379.

In certain embodiments, a nucleic acid sequence of a nucleic acid molecule of the invention is fully complementary to a miR sequence as listed herein, or a precursor thereof. In certain embodiments, a nucleic acid molecule has a nucleobase sequence having one mismatch with respect to the nucleobase sequence of the mature miR, or a precursor thereof. In certain embodiments, a nucleic acid molecule has a nucleobase sequence having two mismatches with respect to the nucleobase sequence of the miR, or a precursor thereof. In certain such embodiments, a nucleic acid molecule has a nucleobase sequence having no more than two mismatches with respect to the nucleobase sequence of the mature miR, or a precursor thereof. In certain such embodiments, the mismatched nucleobases are contiguous. In certain such embodiments, the mismatched nucleobases are not contiguous.

In the context of the present invention any nucleic acid molecule provided comprising a sequence that is complementary to the miR sequence of the invention usually is for impairing the respective miR function and/or expression—thus working as an antisense molecule. On the other hand nucleic acid molecules comprising a sequence identical to the sequence of a given miR of the invention are for use in increasing said miR function and/or expression.

Another aspect of the invention relates to a genetic construct comprising an expressible sequence of a miR as mentioned before, for use in the treatment or prevention of a disease. The disease is preferably selected from a disease as mentioned before, and selected dependent on whether the respective miR is up or downregulated in response to glucocorticoid receptor deficiency.

Another aspect of the present invention provides a method for altering the glucocorticoid activity in a cell, the method comprising the steps of
a. Providing a cell;
b. For decreasing glucocorticoid activity in said cell:
   i. inhibiting the activity of a micro RNA (miR) selected from the group consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-541; or
   ii. increasing the activity of a miR selected from the group consisting of miR-719, miR-483, miR-669j, miR-146a, miR-1948, miR-342-3p, miR-24-2*, miR-132, miR-182, mir-677 and miR-18a; or
c. For increasing glucocorticoid activity in said cell:
   i. increasing the activity of a miR selected from the group consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-541; or
   ii. inhibiting the activity of a miR selected from the group consisting of miR-719, miR-483, miR-669j, miR-146a, miR-1948, miR-342-3p, miR-24-2*, miR-132, miR-182, mir-677 and miR-18a.

In accordance with the present invention in one embodiment said method is for altering the lipid uptake of a cell, wherein the lipid uptake is decreased when the glucocorticoid activity is decreased, and vice versa.

Preferred embodiments of the invention provide the above method, where the activity of a miR is inhibited by introducing into said cell an antisense molecule (antimiR) targeting said miR or a blockmiR targeting the target site of said miR; and/or wherein the activity of said miR is increased by introducing into said cell an expression construct comprising an expressible sequence of said miR.

Preferably said method in some embodiments is an ex-vivo or in-vitro method.

In a preferred embodiment of the invention, in the above method in step b-i and/or step c-i said miR is selected from the group consisting of miR-379, miR-541, miR-127, miR-134, miR-337-5p, miR-382, miR-592, miR-711, miR-762 and mir-2861; preferably wherein said miR is a miR from the miR-379-410 cluster, such as miR-379.

In a preferred embodiment of the invention, in the above method in step b-ii and/or step c-ii said miR is selected from the group consisting of miR-210, miR-221, miR-222, miR-34a and miR-18a.

Said cell of the above method in preferred embodiments is a mammalian cell, most preferably a human cell. Preferably said cell is a liver cell or a fat cell, most preferably said cell is a primary hepatocyte. In some embodiments said cell is not a human embryonic stem cell.

Furthermore, the invention provides a vehicle for the delivery of an inhibitor, or an isolated miR, or a genetic construct of the invention (compounds of the invention). The vehicle of the invention is preferably for assuring the uptake of the compound of the invention at the intended target site in a subject that requires treatment with such a compound. Exemplary delivery vehicles for an oligonucleotide agent featured herein, include lipid (e.g., cationic lipid) containing vehicles (e.g., liposomes), viral containing vehicles (e.g., vectors), polymer containing vehicles (e.g., biodegradable polymers or dendrimers), and peptide containing vehicles (e.g., a penetration peptide), exosomes, and bacterially-derived, intact minicells. In a preferred example the delivery vehicle includes more than one component. For example, it can include one or more lipid moieties, one or more peptides, one or more polymers, one or more viral vectors, or a combination thereof. Preferred embodiments pertain to a delivery vehicle which is an association complex such as a liposome. A liposome generally includes a plurality of components such as one or more of a cationic lipid (e.g., an amino lipid), a targeting moiety, a fusogenic lipid, a PEGylated lipid. In some embodiments, the PEG-lipid is a targeted PEG-lipid. For example, a liposome can include a nucleic acid and an amine-lipid and a PEGylated lipid. In some embodiments, the PEG-lipid is a targeted PEG-lipid. In some embodiments, the preparation also includes a structural moiety such as cholesterol. Most preferred in context of the present invention is a viral delivery vehicle, in particular a virus specifically targeting fat and/or liver cells.

Delivery is preferably conducted by a viral vector. The viral vector may be retrovirus, such as a lentivirus, or an adenovirus. Thus, the invention provides a viral vector, comprising an inhibitor of a miR or an isolated miR of the invention (sequences of the invention). These sequences may inserted into an untranslated region of a gene, the gene being part of a construct or cassette which is then delivered by the vector. When transduced, a host cell will express the sequence of the invention and therefore silence or express any miR of the present invention. The vector is preferably the viral capsid and does not comprise any viral or other polynucleotides, other than the present construct.

The invention in another aspect provides a pharmaceutical composition comprising an inhibitor (antimiR or blockmiR), an isolated miR molecule, a genetic construct or a vehicle, such as a viral vector, according to the various embodiments of the invention, together with pharmaceutically acceptable carriers and/or excipients.

Also provided is the use of the inhibitor of a miR (antimiR or blockmiR), an isolated miR-molecule or a genetic construct according to the various embodiments of the invention, in the manufacture of a medicament for the hereinabove mentioned diseases.

Provided herein in congruence with the present invention is a pharmaceutical composition, comprising nucleic acid molecules (oligonucleotides) of the invention. In certain embodiments, such pharmaceutical compositions are used for the treatment of disorders dependent on glucocorticoid signaling, in particular glucocorticoid excess such as metabolic disorders, and associated conditions. In certain embodiments, a pharmaceutical composition provided herein comprises a compound comprising an oligonucleotide consisting of 12 to 30 linked nucleosides and having a nucleobase sequence complementary to the miR of the invention, preferably to the miR-379-410 cluster, most preferably to miR-379, or a precursor thereof. In certain embodiments, a pharmaceutical composition provided herein comprises a compound consisting of an oligonucleotide consisting of 12 to 30 linked nucleosides and having a nucleobase sequence complementary to a miR of the invention, preferably to the miR-379-410 cluster, most preferably to miR-379, or a precursor thereof.

Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

One further aspect of the present invention pertains to a method of treating or preventing a disease in a subject in need thereof, the method comprising administering to said subject a therapeutically effective amount of an inhibitor of an miR, an antimiR or blockmiR, an isolated miR molecule or a genetic construct according to the various embodiments of the invention.

Provided is also a method of alleviating the adverse or side effects of a glucocorticoid therapy, the method comprising the administration of an inhibitor of a miR selected from the group consisting of miR-331-5p, miR-378*, miR-210, miR-152, miR-676*, mir-187, miR-1981, miR-203, miR-337-5p, miR-221, miR-222, miR-31*, miR-29b, miR-676, miR-34a, miR-383, miR-379, miR-301a, miR-1274a, miR-134, miR-409-5p, miR-431, miR-382, miR-127 and miR-541; preferably selected from the group miR-379, miR-541, miR-127, miR-134, miR-337-5p, miR-382, miR-592, miR-711, miR-762 and mir-2861; more preferably wherein said miR is a miR from the miR-379-410 cluster, such as miR-379.

Glucocorticoids may be used in low doses in adrenal insufficiency. In much higher doses, oral or inhaled glucocorticoids are used to suppress various allergic, inflammatory, and autoimmune disorders. Inhaled glucocorticoids are the second-line treatment for asthma. They are also administered as post-transplantory immunosuppressants to prevent the acute transplant rejection and the graft-versus-host disease. Glucocorticoid treatment or excess is associated with various adverse effects which include amongst others hyperglycemia due to increased gluconeogenesis, insulin resistance, and impaired glucose tolerance, weight gain due to increased visceral and truncal fat deposition (central obesity) and appetite stimulation.

Preferred embodiments thus pertain to treatments wherein the above inhibitor of the miR of the invention is administered in combination with a glucocorticoid.

BRIEF DESCRIPTION OF THE FIGURES

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIGS. 3A-3H: MicroRNA-379 controls systemic triglyceride levels via the lipolysis-stimulated lipoprotein receptor (Lsr). (3A) Vertebrate-conserved, miR-379 binding site in the coding sequence of the Lsr mRNA as predicted by RNA22. Flag-Lsr protein levels in response to miR-379 mimics transfected into Hek293 cells. (3B) Protein levels of Lsr from livers of animals treated with anti-379 LNA or scrambled control (n=5 per group), same animals as in FIG. (2A). (3C) Protein levels of Lsr from livers of wild-type mice treated with dexamethasone (1 mg/kg BW) or isotonic saline for 28 days. (3D) Western blot of liver extracts from wt or LDLRKO mice treated with control or LSR shRNA-containing adenovirus and with anti-miR-379 or scrambled control LNA (n=7). (3E) Serum triglyceride levels of same animals as in E under fed conditions. (3F) Flag-LSR protein levels in Hek293 cells treated with miR-379 mimics. 100 nM cel-miR-293b was used as the control mimic. [-]: untransfected. (3G-3H), miR-379 target validation of LSR (3G) and LDLR (3H) using a dual-luciferase reporter gene assay. miRNA binding site (MBS) predicted by RNA22 and MiRTiF and the corresponding mutated (mut) sequence were cloned into psiCHECK™-2 vector. Bar and line graphs show mean±SEM; ANOVA (with post-hoc test): *$p<0.001$, $p<0.01$, or *$p<0.05$.

FIGS. 5A-5C: (5A), Hepatic miR-379 levels in wild-type mice treated with negative control (NC) and GR-specific miRNA AAV (n=4 per group). (5B), Hepatic miR-379 levels in wild-type and hepatocyte-specific GR knockout mice (n=4 per group). (5C), Quantitative miR-379 PCR levels in primary hepatocytes treated with 1 µM dexamethasone or vehicle (2% EtOH in PBS) for 9 h. Data are mean±SEM, t-test or ANOVA (with post-hoc test): *$p<0.001$, $p<0.01$, or *$p<0.05$.

FIGS. 6A-6J: (6A), Serum alanine aminotransferase (ALT) levels in mice treated with anti-379 locked-nucleic acid (LNA) or scrambled control (n=5 per group). (6B-6D), Liver Glycogen, triglyceride, and cholesterol of animals in (6A). (6E), Cholesterol content of eluates from FPLC-fractionated serum of animals in (6A). (6F-6G), Fasting blood glucose and HOMA-IR of animals in (6A). (6H), Serum ALT levels in mice treated with recombinant adeno-associated (rAAV) negative control (NC) virus or rAAV for miR-379 overexpression (n=4 per group). (6I-6J), Serum cholesterol and cholesterol in eluates from FPLC-fractionated serum of animals in (6H). Except for FPLC, data are mean±SEM, t-test or ANOVA (with post-hoc test): *$p<0.001$, $p<0.01$, or *$p<0.05$.

EXAMPLES

Example 1: miR Relevant in Metabolic Dysfunction

Figure 1A:
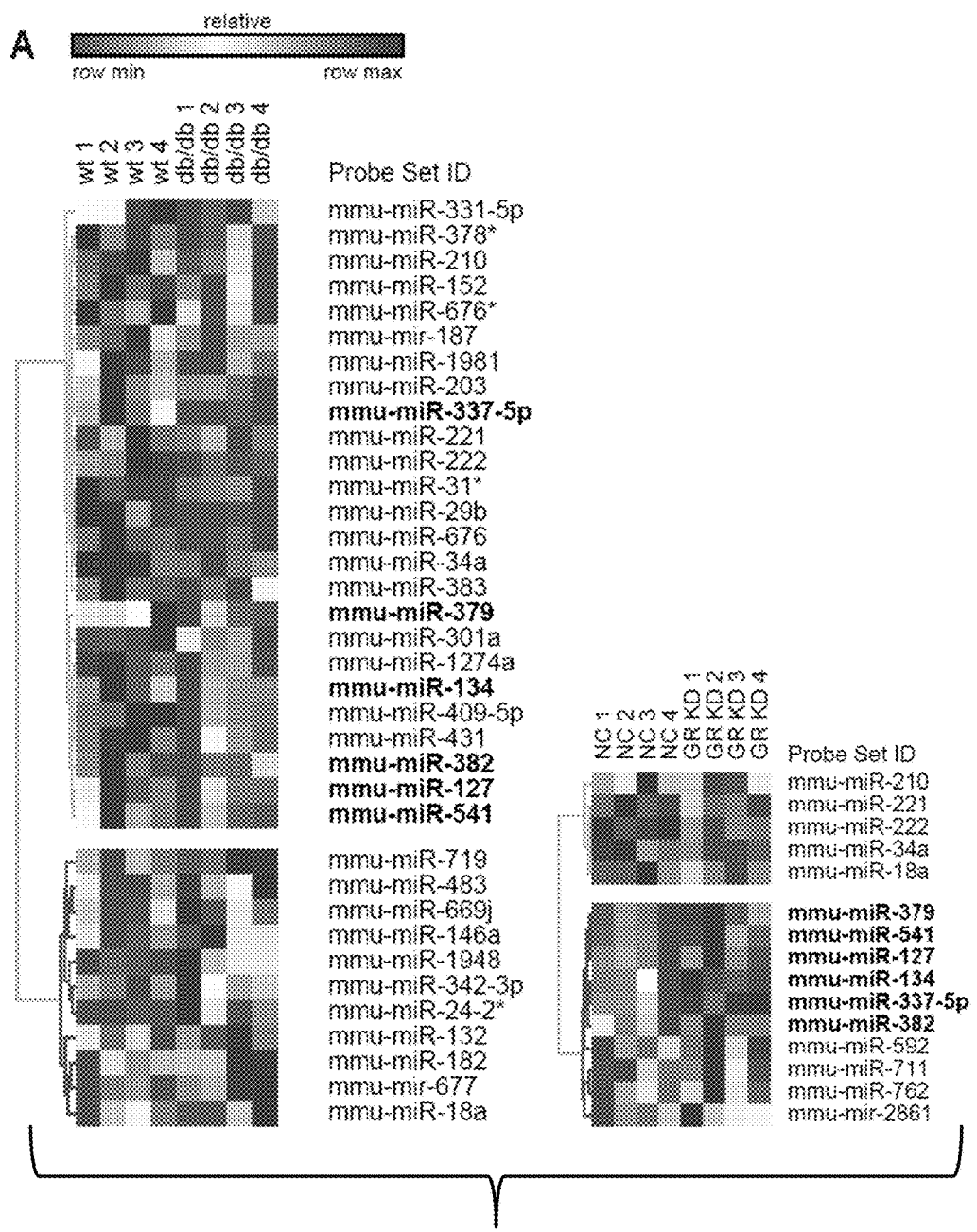
FIGS. 1A-1F: The miR-379/410 cluster is a downstream target of glucocorticoid signaling. (1A) Heatmap showing relative miRNA expression between wild-type (wt) and db/db mice (n=4); and between mice treated with negative control (NC) and GR-specific miRNA recombinant adeno-associated virus (rAAV) (n=4). Higher and lower expression is displayed in red and green, respectively. Commonly regulated miRNAs in the miR-379/410 cluster are shown in bold. Differentially regulated miRNAs are ≥2-fold, p<0.05. (1B) Quantitative miR-379 PCR levels in livers of db/db, New Zealand Obese (NZO) mice, and corresponding controls—wt and New Zealand Black (NZB) (n≥4). (1C) Quantitative miR-379 levels in livers of db/db mice treated with control or GR-specific shRNA adenovirus (n=5). (1D) Hepatic miR-379 levels as determined by RT-qPCR analysis in wt and hepatocyte-specific GR knockout mice (GR-AlfpCre) (n=4). (1E) Chromatin immunoprecipitation (ChIP) qPCR for validation of GR binding regions (GBR) upstream miR-379 hairpin: 1 (−11197 to −111268), 2 (−21021 to −21135), and 3 (−26761 to −26793). Fold enrichment of GR binding site occupancy relative to negative control, anti-HA. (n=4). (1F) miR-379 levels in human liver treated ex vivo with or without 1 μM RU486 and 0.1 μM DEX (n=4). snoRNA-202 was used for normalization of miRNA levels. Bar graphs show mean±SEM; t-test or ANOVA (with post-hoc test): *p<0.001, p<0.01, or *p<0.05.

To define GC/GR-dependent miRNA networks with immediate relevance in metabolic dysfunction, the inventors initially performed large-scale miRNA expression profiling in livers from wild-type and db/db diabetic mice as a model for diabesity-related hyperglucocorticoidemia (Lemke et al., 2008). A total of 36 miRNAs was found to be up- or down-regulated more that 2-fold between these animals, thereby validating our experimental setup (FIG. 1A). Next, the inventors crossed this data set with a second miRNA signature, resulting from differential expression profiling between mice lacking the GR specifically in hepatocytes and control littermates (Rose et al., 2011). Data cross-comparison revealed a set of 10 miRNAs that showed significant down-regulation in response to GR deficiency and simultaneous induction in diabesity (FIG. 1A), indicating that these miRNAs represent bona fide mediators of GC/GR-driven metabolic dysfunction. Intriguingly, 6 out of 10 GC/GR-targeted miRNAs are located in the 379-410 miRNA cluster that is conserved between all mammalian species (Benetatos et al., 2013; Luk et al., 2011), and resides on mouse and human chromosomes 12 and 14, respectively. Indeed, selective expression analysis verified the induction of all 5 cluster members in db/db mice by quantitative PCR (data not shown).

Figure 1B:
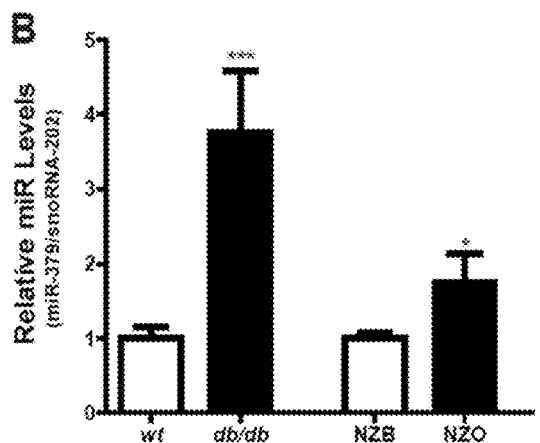
Figure 1C:
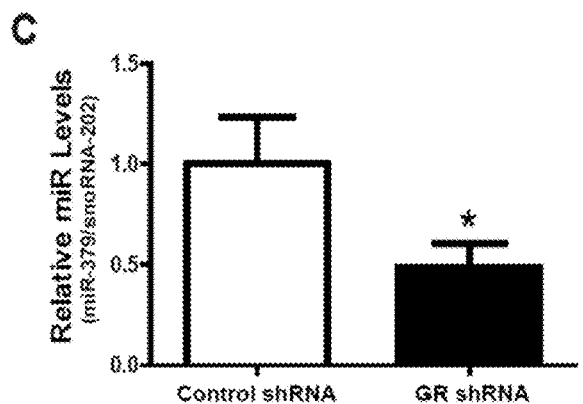
Figure 1D:
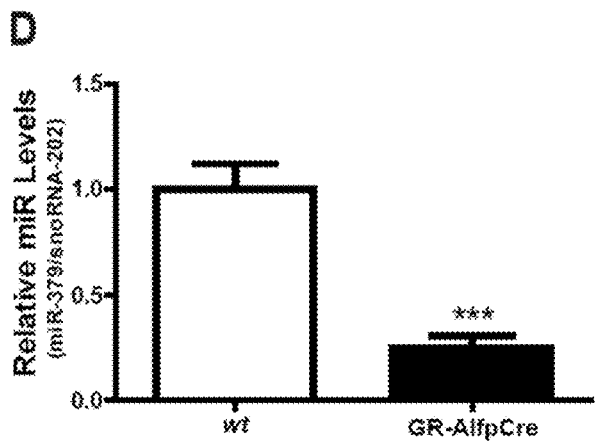

The most substantial 4-fold induction of miRNA379 in diabetic mice (FIG. 1B) next prompted the inventors to investigate the general importance of this regulation in other models of elevated GC action. To this end, we analyzed liver extracts from healthy New Zealand Black (NZB) mice compared to New Zealand obese (NZO) mice, the latter representing a multigenic obesity model (Leiter and Reifsnyder, 2004). In congruence with the hyperglucocorticoidemia in this model, miR-379 expression was found to be elevated significantly when compared to corresponding controls (FIG. 1B), thereby correlating with circulating corticosterone levels in these mice (not shown), supporting the hypothesis that particularly miR-379 is a key output of the GC/GR endocrine pathway under conditions of metabolic dysfunction. In support of this possibility, levels of miR-379 were consistently found to be diminished in models of GR deficiency, including both miRNA-induced and genetic hepatocyte-specific GR deficiency (FIG. 1C, 1D).

Figure 1E:
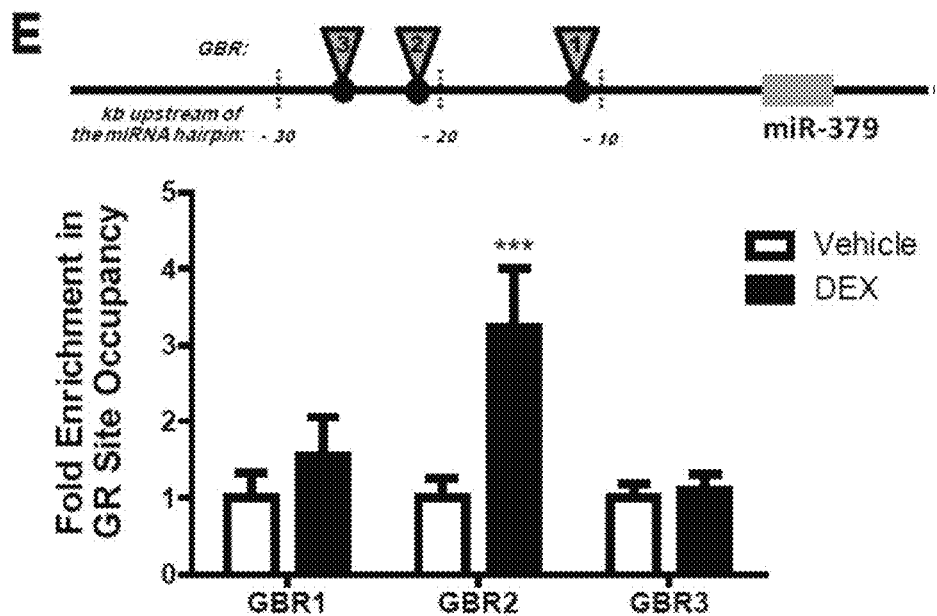

Indeed, chromatin immunoprecipitation using GR-specific antibody experimentally verified the recruitment of the receptor to a binding site within the miR-379 promoter (FIG. 1E). A similar result had been previously reported in GR Chip-sequencing data deposited in human genome database suggesting that the miR-379/410 cluster represents a direct transcriptional target of the GR.

Figure 1F:
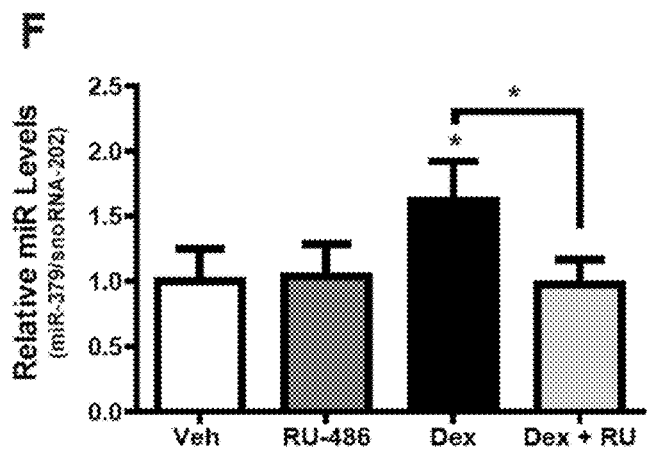

To verify the functional significance of GR DNA binding to the miR-379 locus in vivo, we examined mice harboring a dimerization-defective GR mutant (GRdim) that impairs receptor DNA binding to full GREs. Wild-type mice chronically treated with DEX exhibited higher hepatic levels of miR-379 as compared with controls, while the genetic impairment of GR DNA-binding capacity in GRdim mice completely abrogated this effect, thereby validating a DNA-binding-dependent regulatory function of the GC/GR pathway for miR-379 expression in the liver. Of note, DEX treatment of isolated primary mouse hepatocytes and human liver slices (FIG. 1F) led to the induction of miR-379 irrespective of culture glucose levels (data not shown), demonstrating the cell autonomy of the observed effects. Co-treatment with the GR-antagonist RU-486 completely abolished the DEX effects thereby confirming GR-specificity (FIG. 1F).

Example 2: MicroRNA-379 Controls Systemic VLDL Triglyceride Levels

Figure 2A:
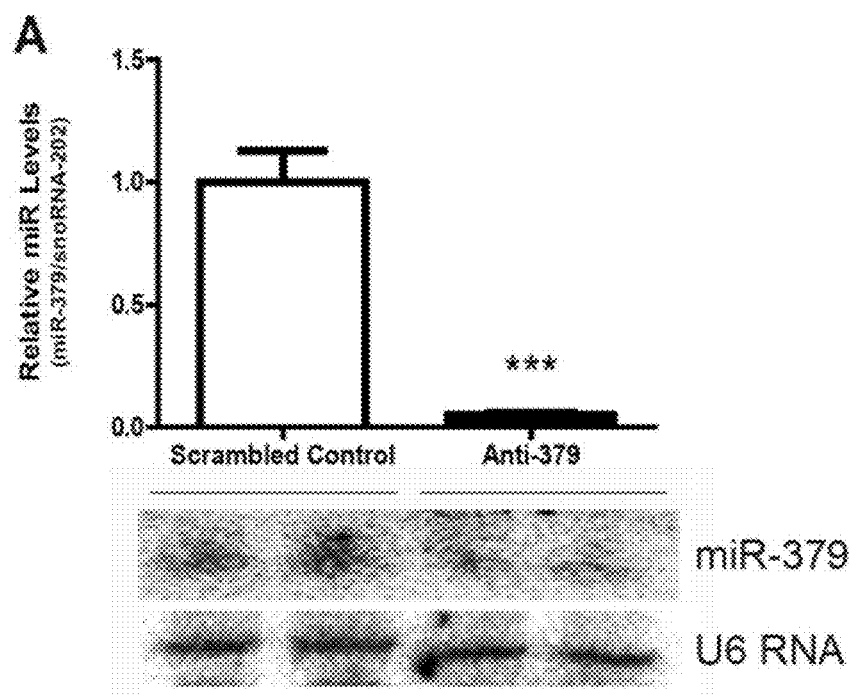
FIGS. 2A-2F: MicroRNA-379 controls systemic VLDL triglyceride levels. (2A) RT-qPCR levels and northern blot of miR-379 in mice treated with anti-379 locked-nucleic acid (LNA) or scrambled control (n=5 per group). (2B) Serum triglyceride and cholesterol levels after 1 and 2 weeks of LNA treatment of animals in (2A). (2C) Triglyceride content of eluates from FPLC-fractionated serum of animals in (2A). (2D) Northern blot of miR-379 in mice treated with isotonic saline, recombinant adeno-associated (rAAV) negative control (NC) virus or rAAV for miR-379 overexpression (n=4 per group). (E) Serum triglycerides of animals in (2D). (2F) Triglyceride content of eluates from FPLC-fractionated serum of animals in (2D). For A, B & E, data are mean±SEM, t-test or ANOVA (with post-hoc test): *p<0.001, p<0.01, or *p<0.05.
Figure 2B:
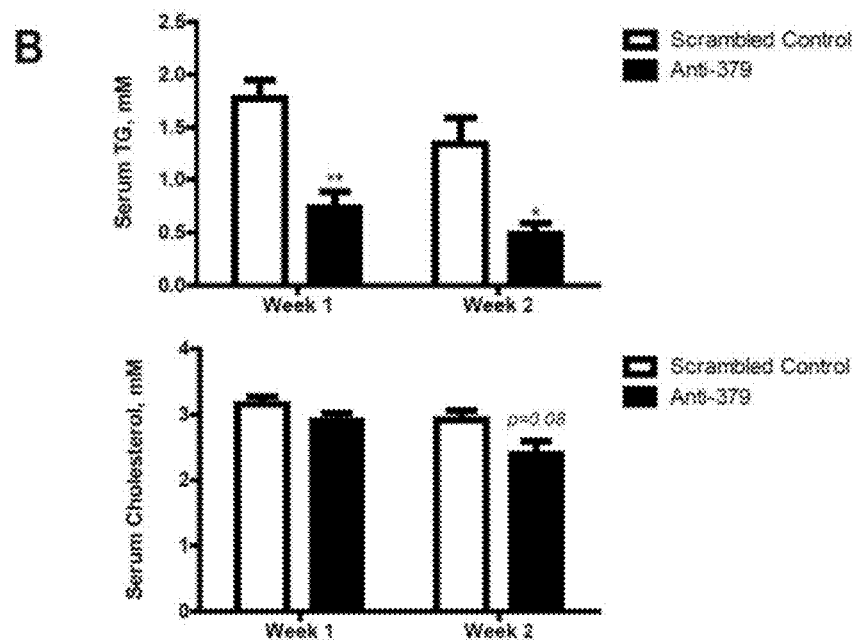

These results thus far identified miRNA379 as a direct target of GC/GR signaling with aberrant hepatic expression in diabesity, prompting the inventors to next explore the functional importance of miRNA379 for hepatic and systemic energy homeostasis. To this end, the inventors efficiently silenced miRNA379 predominantly in the liver by locked nucleic acid (LNA) antisense technology in wild-type animals (FIG. 2A). While miRNA379-specific LNA delivery had no influence on liver toxicity markers (FIG. 6A), hepatic glycogen (FIG. 6B), liver TG (FIG. 6C), and cholesterol (FIG. 6D) levels, miRNA379 deficiency significantly lowered total serum TG levels (FIG. 2B). Total serum cholesterol remained largely unaffected (FIG. 2B), overall indicating that hepatic miRNA379 specifically controls circulating TG metabolism.

Figure 2C:
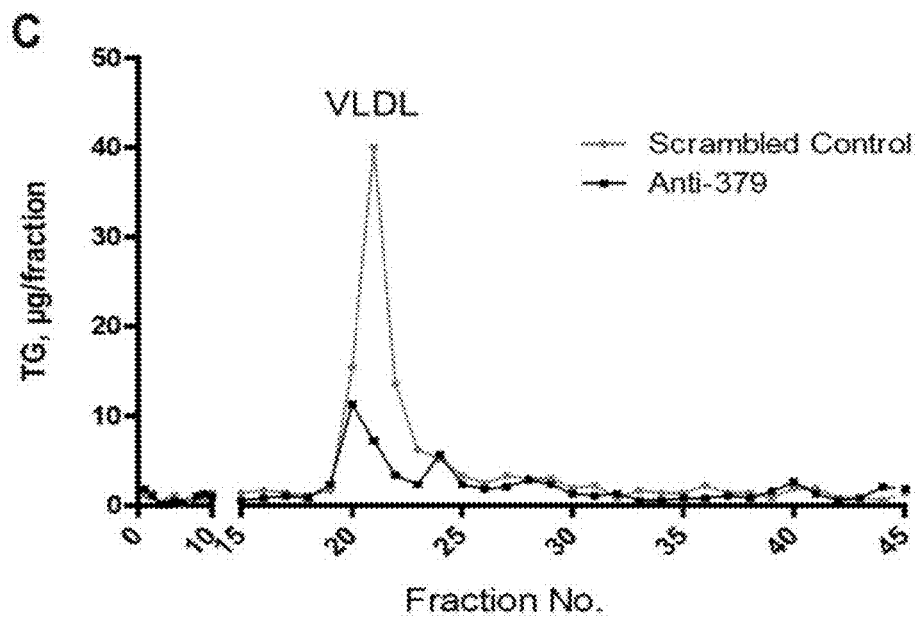
Figure 6E:
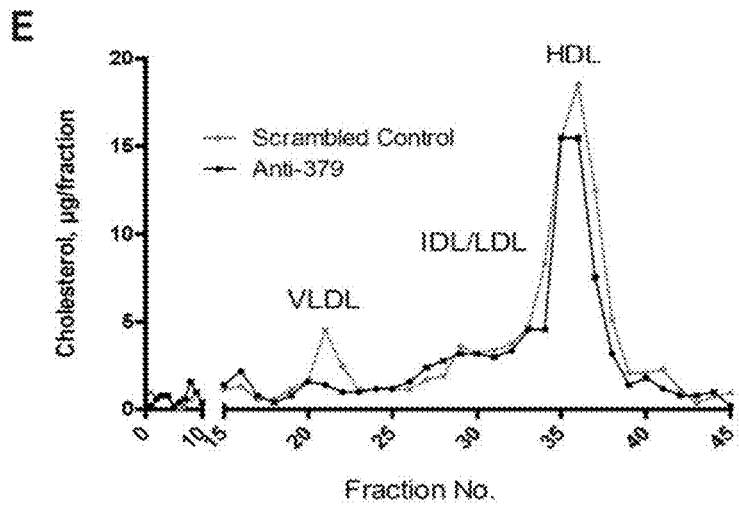
Figure 6F:
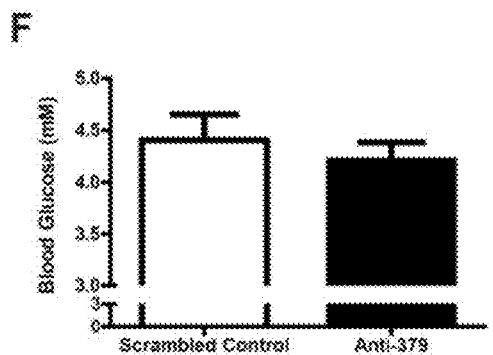
Figure 6G:
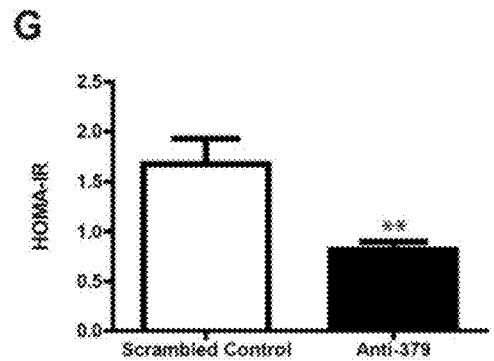

Indeed, fast protein liquid chromatography (FPLC)-mediated fractionation studies revealed that liver silencing of miRNA379 robustly impaired levels of VLDL-associated TG, while leaving cholesterol lipoprotein loading intact (FIGS. 2C, 6E). Consistent with the role of elevated VLDL-TG as the main risk factor for cardiovascular complications in the Metabolic Syndrome and its tight association with insulin resistance (Chahil and Ginsberg, 2006), diminished VLDL-TG in miRNA379 LNA-treated mice had no effect on blood glucose levels (FIG. 6F) but improved insulin resistance (FIG. 6G).

Figure 2D:
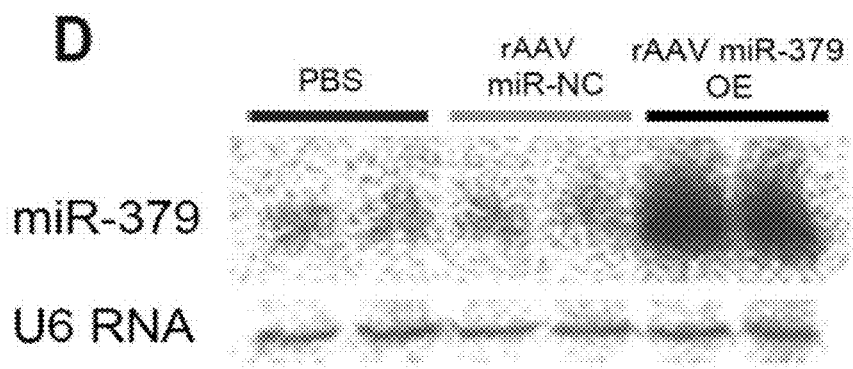
Figure 2E:
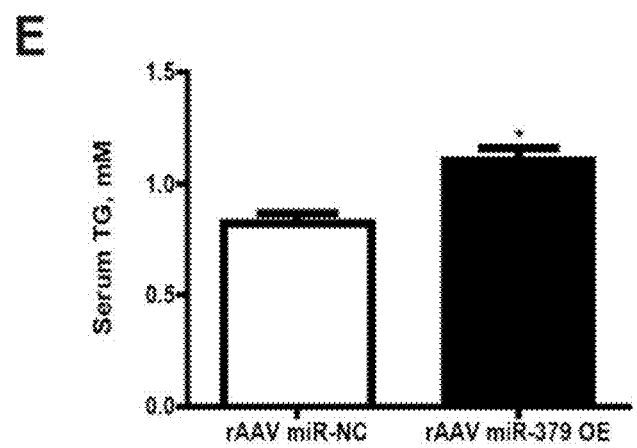
Figure 2F:
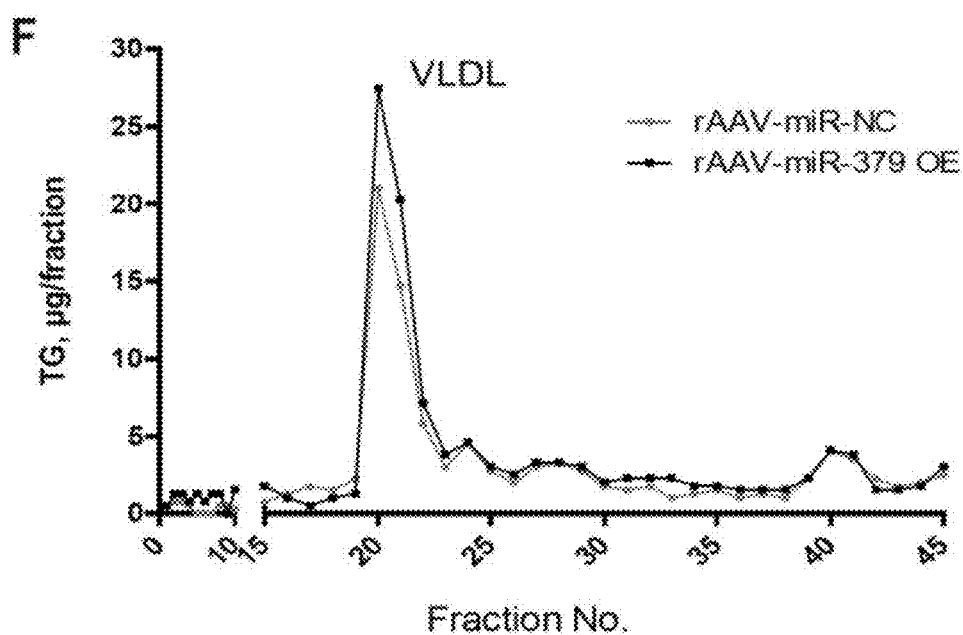
Figure 6H:
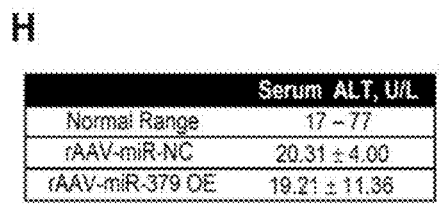
Figure 6I:
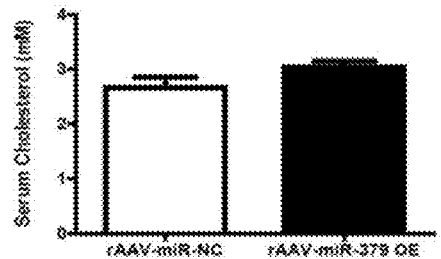
Figure 6J:
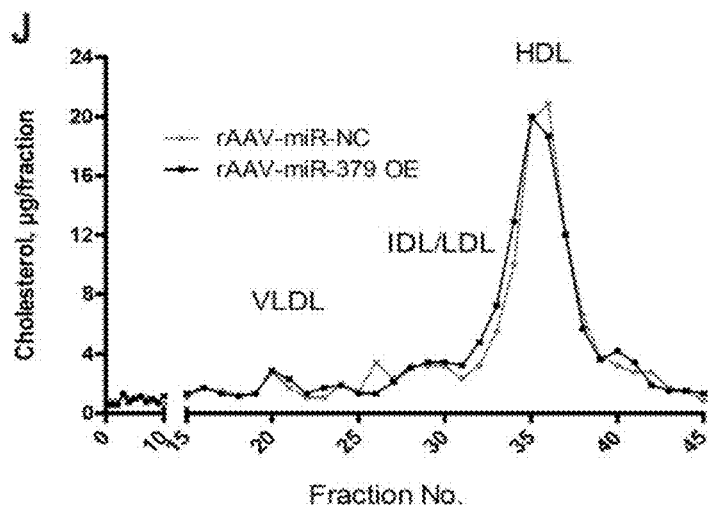

To next determine whether elevation of hepatic miRNA379 expression was sufficient to cause systemic dyslipidemia in a more chronic setting, the inventors employed a novel adeno-associated virus (AAV) delivery system allowing the expression of miRNAs specifically in liver parenchymal cells but not in other liver cell types for a period of several months (Kulozik et al., 2011). Eight weeks after AAV delivery, mice with hepatocyte-specific miRNA379 over-expression (FIG. 2D) that did not affect liver damage markers (FIG. 6H) displayed significantly higher levels of serum TG associated with the VLDL fraction (FIG. 2E, 2F) but maintained normal cholesterol homeostasis (FIGS. 6I, 6J).

Example 3: MicroRNA-379 Controls Systemic Triglyceride Levels Via the Lipolysis-Stimulated Lipoprotein Receptor (Lsr)

Figure 7A:
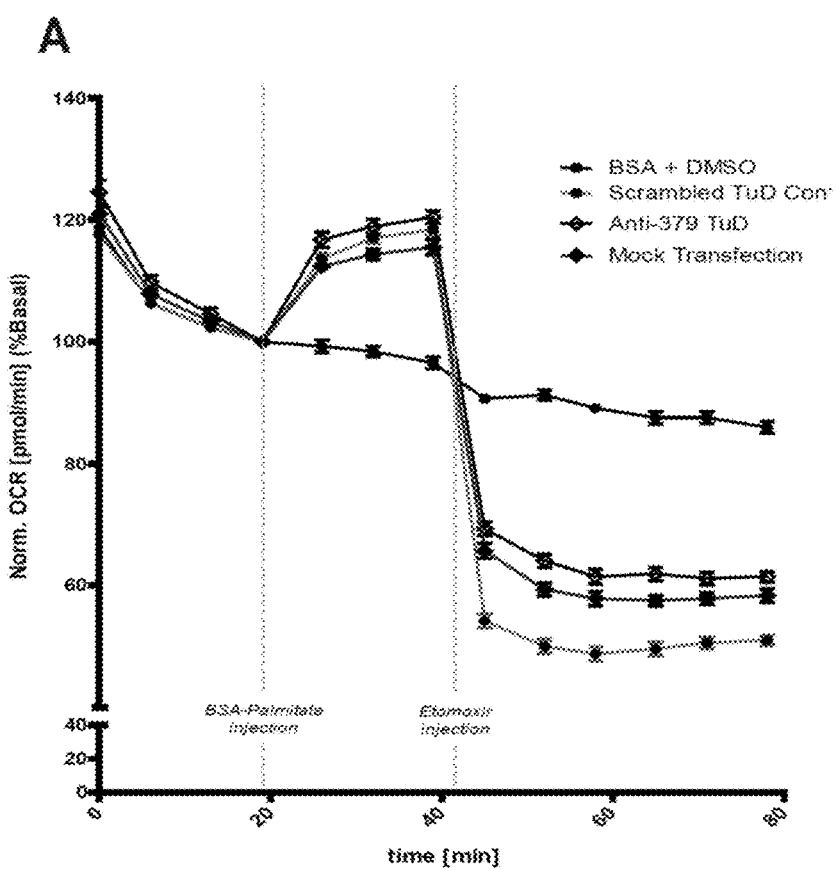
FIGS. 7A-7C: (7A) Normalized oxygen consumption rate (OCR) of Hepa1-6 cells treated with anti-miR-379 tough decoy construct or scrambled control (n=8 per group). Data generated using XF96 Extracellular Flux Analyser (Seahorse). (7B) Abdominal white adipose tissue lipoprotein lipase (LPL) activity in mice treated with anti-379 locked-nucleic acid (LNA) or scrambled control (n=5 per group). (7C) Hepatic VLDL release in mice treated with anti-379 locked-nucleic acid (LNA) or scrambled control (n=5 per group). Data are mean±SEM, t-test or ANOVA (with post-hoc test): *$p<0.05$.
Figure 7B:
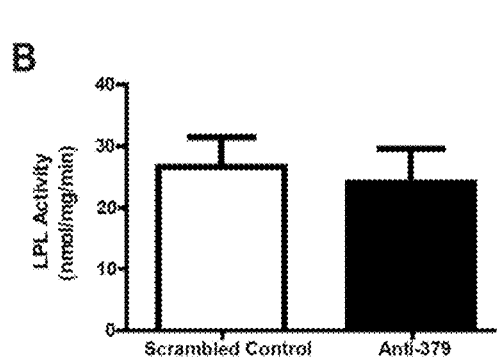
Figure 7C:
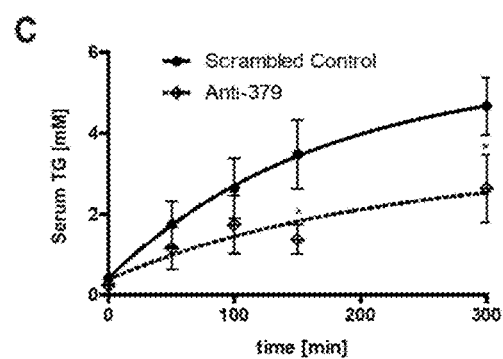

The observed specificity of miRNA379 for the regulation of serum VLDL-TG next prompted the inventors to explore the mechanistic basis of this effect. Systemic TG metabolism is determined by the relative balance of hepatic and peripheral lipid uptake and release, correlating with de novo TG formation (lipogenesis) and fatty acid (FA) β-oxidation in the liver (Kersten et al., 1999). In this respect, miRNA379-specific LNA treatment of mouse hepatocytes had no influence on FA oxidation as determined by metabolic flux analysis (FIG. 7A), and circulating levels of total ketone bodies as an output measure for the FA oxidation pathway remained unaltered between miRNA379 LNA and non-specific control LNA-treated mice (data not shown). Also, peripheral adipose lipoprotein lipase activity was unaffected by miRNA379 deficiency (FIG. 7B), while hepatic VLDL release was slightly reduced as compared with control littermates (FIG. 7C). These data suggested that the control of circulating VLDL-TG by hepatic miRNA379 is not conferred by alterations in hepatic or peripheral lipid synthesis or degradation pathways.

Figure 3A:
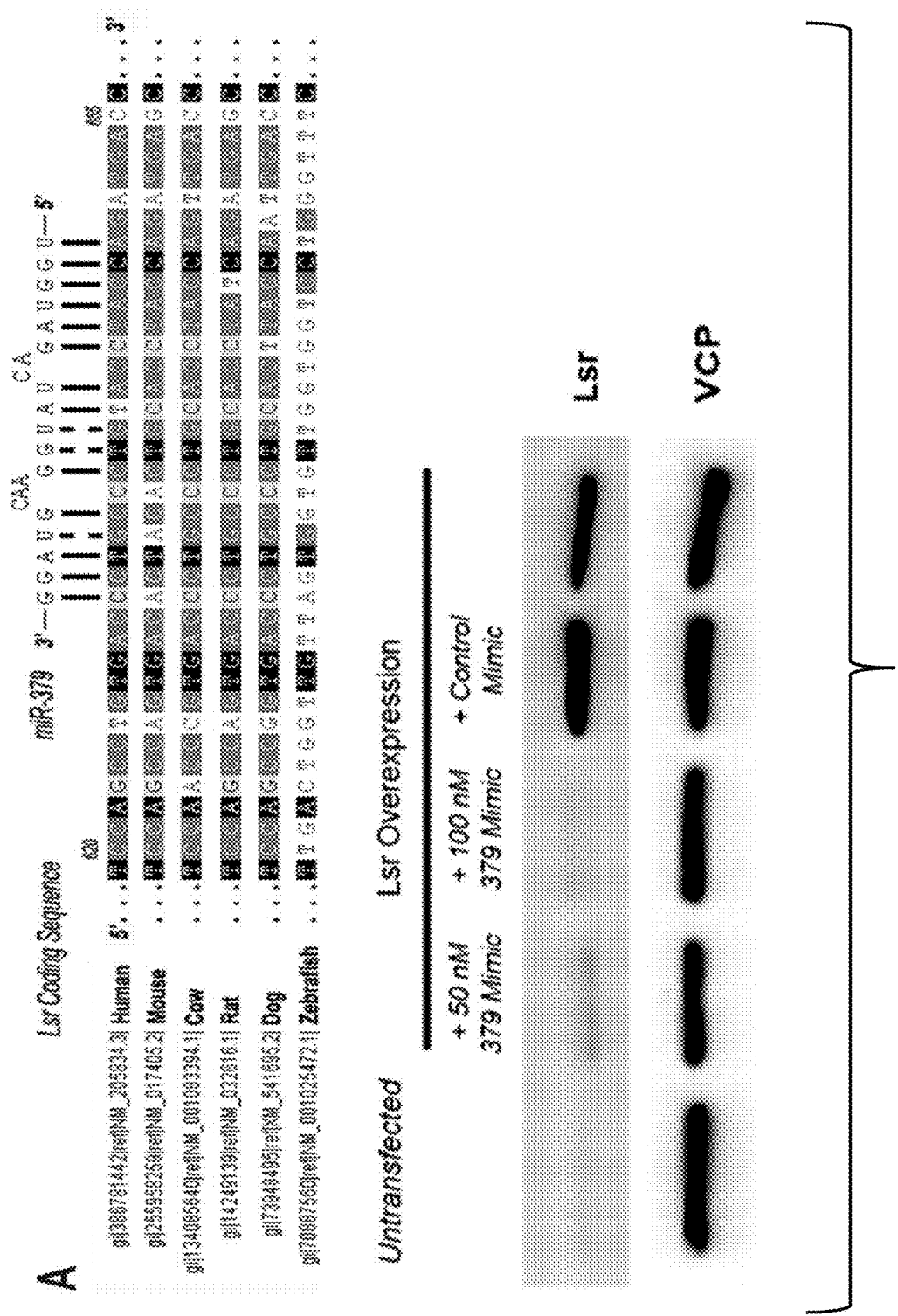

In contrast, bio-informatic miRNA target gene screening revealed that miRNA379 was predicted to bind genes involved in hepatic lipid (re-) uptake, most notably including the major hepatic lipid re-uptake transporters lipolysis-stimulated lipoprotein receptor (LSR) and low-density lipoprotein receptor (LDLR) (FIG. 3A). Both, LSR and LDLR expression has previously been found to be severely compromised in hypertriglyceridemic db/db mice, and liver-specific inactivation of LSR triggered the elevation of VLDL-TG in healthy wild-type animals by specifically preventing hepatic re-uptake of Apolipoprotein B-associated TG from the circulation (Narvekar et al., 2009).

In line with the in-silico predictions and a direct silencing effect of miRNA379 on an LSR transcript (FIG. 3A), LNA-mediated miRNA379 silencing led to the up-regulation of hepatic LSR and LDLR protein expression in wild-type animals (FIG. 3B), and DEX treatment inhibited LSR and LDLR protein levels as compared with controls (FIG. 3C), overall suggesting that miRNA379 may—at least in part—regulate systemic VLDL-TG through its inhibitory impact on the LSR-LDLR pathway.

To address this issue directly, the inventors performed genetic rescue experiments in wild-type mice by first preventing the miRNA379 LNA-dependent induction of LSR protein expression through simultaneous shRNA-mediated inhibition of LSR by LNA/shRNA adenovirus co-administration. 10 days after LNA/adenovirus co-delivery into the tail vein of mice, miRNA379 silencing triggered hypotriglyceridemia while LSR inhibition alone caused an elevation of circulating VLDL-TG as described when compared with control littermates (FIG. 2). Of note, both treatments left cholesterol parameters unaffected. Intriguingly, in the absence of functional hepatic LSR, miRNA379 silencing still exerted an effect on total and VLDL-associated serum TG levels, suggesting that LSR alone does not explain the impact of miRNA379 on systemic TG metabolism. Consistent with this assumption, LDLR protein levels were significantly increased upon double miRNA379/LSR knockdown.

Figure 3F:
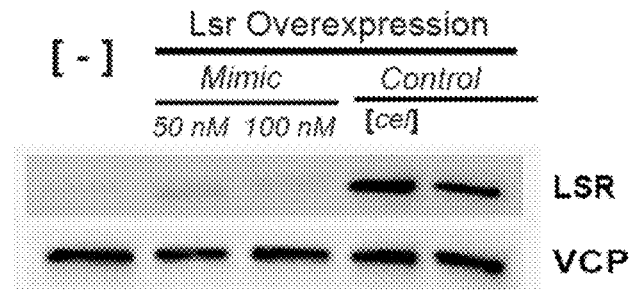
Figure 3G:
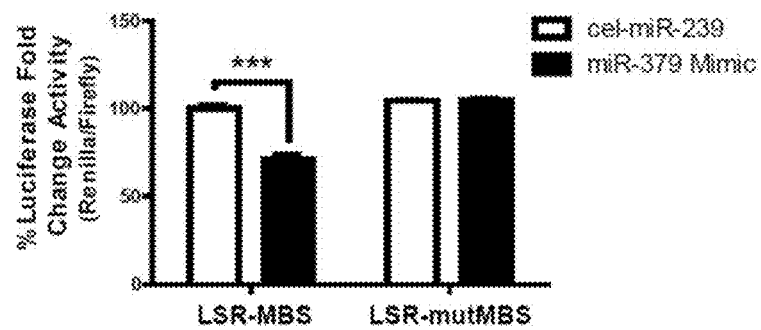
Figure 3H:
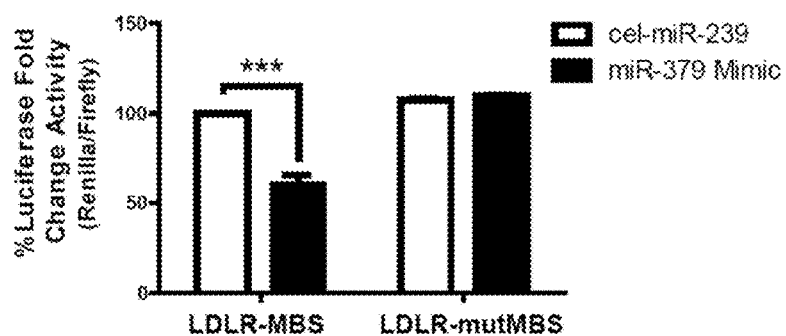

To test for a potential compensatory role of LDLR in the absence of LSR, we next employed wild-type and LDLR knockout (KO) animals in LNA/LSR shRNA adenovirus co-injection experiments to obtain a functional LSR/LDLR double deficiency in the liver (FIG. 3D). While miR-379 silencing reduced serum TG in both wild-type and LDLRKO mice (FIG. 3E), the effect of miR-379 LNA delivery was completely abrogated in LDLR/LSR double-deficient mice (FIG. 3E), overall demonstrating that miR-379 determines circulating TG levels through a double impact on two components of hepatic TG clearance, i.e. LSR and LDLR. Consistent with this notion, treatment of cultured cells with miR-379 mimics inhibited both protein expression (FIG. 3F) and luciferase reporter genes carrying wild-type LSR and LDLR miR-379 target sequences, while leaving mutated target sites unaffected (FIG. 3G, 3H), thereby validating the specificity of the observed effects.

Example 4: Inhibition of miR-379 Counteracts Hypertriglyceridemia in Diabetic-Obese Mice Antisense strategies targeting specific miRNAs have emerged as attractive therapeutic options for several human pathologies, including metabolic complications and viral diseases, thus recently prompting first clinical trials in this direction (Stenvang et al., 2012). Given the current search for efficient and specific therapeutic modalities to overcome hypertriglyceridemia as the major cardio-vascular risk factor in patients with the Metabolic Syndrome (Rosenson and Underberg, 2013), it was an object address the therapeutic potential of miRNA379 in diabesity-associated hyperlipidemia.

Figure 4A:
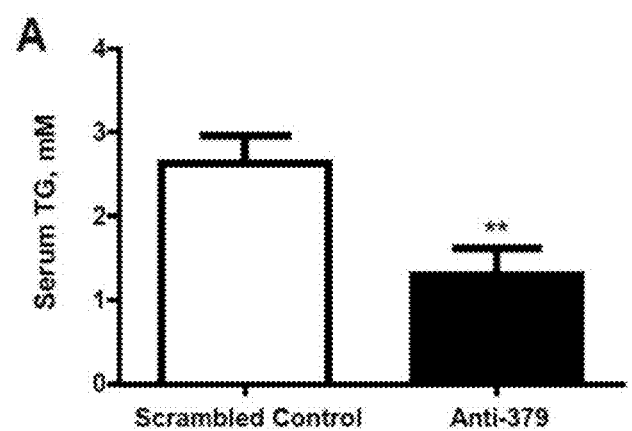
FIGS. 4A-4I: Inhibition of miR-379 counteracts hypertriglyceridemia in diabetic-obese mice. (4A) Serum triglyceride levels of db/db mice treated with anti-379 LNA or scrambled control (n=7 per group). (4B), Homeostatic Model Assessment for Insulin Resistance (HOMA-IR) of animals in (4A). (4C) Triglyceride content of eluates from FPLC-fractionated serum of animals in (4A). (4D), Protein levels of Lsr from livers of animals in (4A). For (4A) and (4B), data are mean±SEM, t-test: *$p<0.001$, $p<0.01$, or *$p<0.05$. (4E) Triglyceride profiles of FPLC-fractionated serum of NZO mice treated with anti-miR-379 or scrambled control LNA (n=7). VLDL peak is indicated. (4F) Protein levels of LSR and LDLR from livers of same animals as in 4E. (4G) Protein levels of LSR and LDLR from livers of db/db mice treated with an anti-miR-379 or scrambled control Tough Decoy (TuD) construct delivered by rAAV 28 days postinjection (n=8). (4H) Triglyceride profiles of FPLC-fractionated serum of same animals as in G under fed conditions. VLDL peak is indicated. (4I) Triglyceride profiles of FPLC-fractionated serum of C57Bl/6J mice fed with low-fat (10%) or high-fat (60%) diet for 12 weeks and treated with either anti-miR-379 or scrambled control Tough Decoy (TuD) construct delivered by rAAV. Mice were sacrificed four weeks after virus injection at 18 weeks of age. VLDL peak is indicated.
Figure 4B:
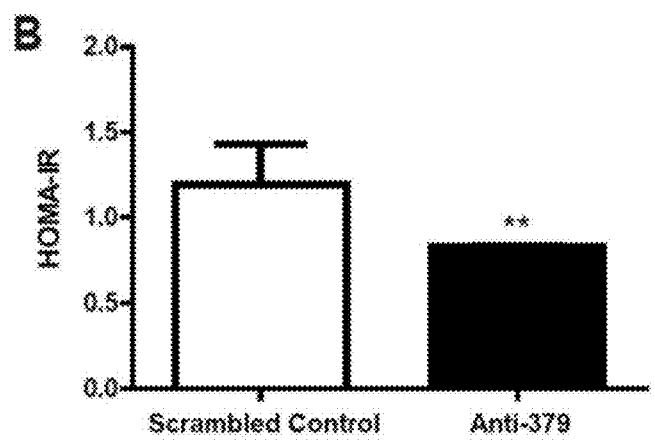
Figure 4C:
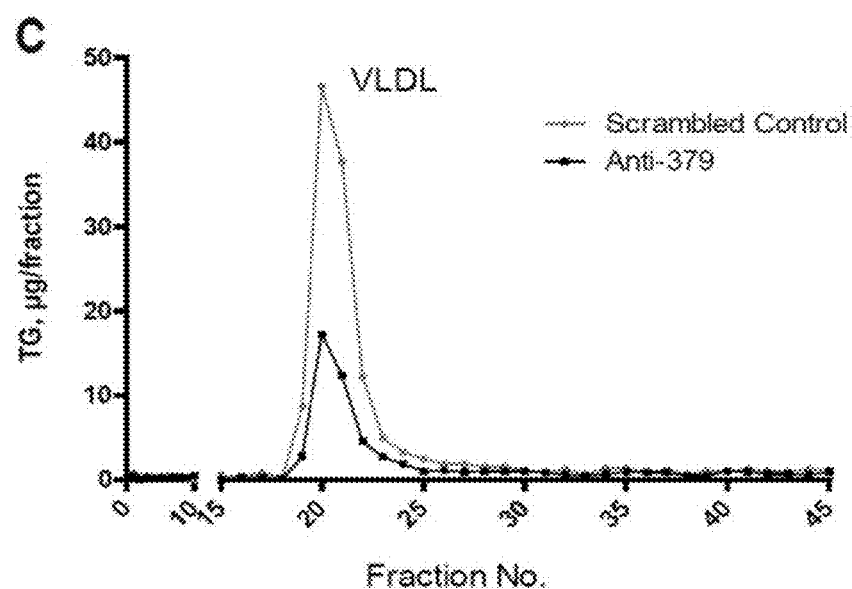
Figure 4D:
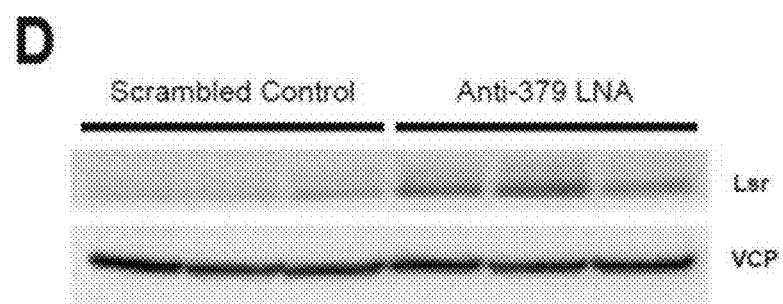
Figure 8A:
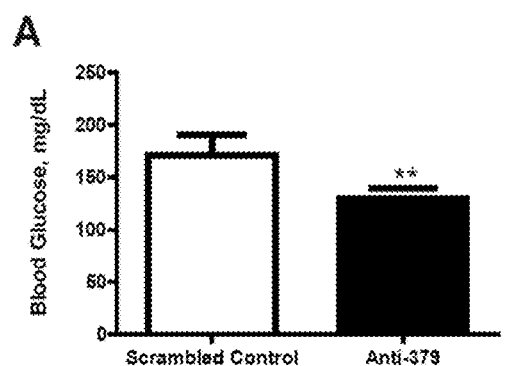
FIGS. 8A-8D: (8A) Fasting blood glucose levels of db/db mice treated with anti-379 LNA or scrambled control (n=7 per group). Data are mean±SEM, t-test: $p<0.01$. (8B-8C) Serum Cholesterol and cholesterol in eluates from FPLC-fractionated serum of animals in (8A). (D) Liver sections stained with oil red O and hematoxylin from representative animals in (8A**).
Figure 8B:
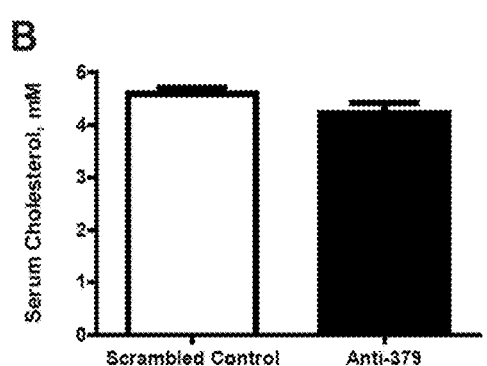
Figure 8C:
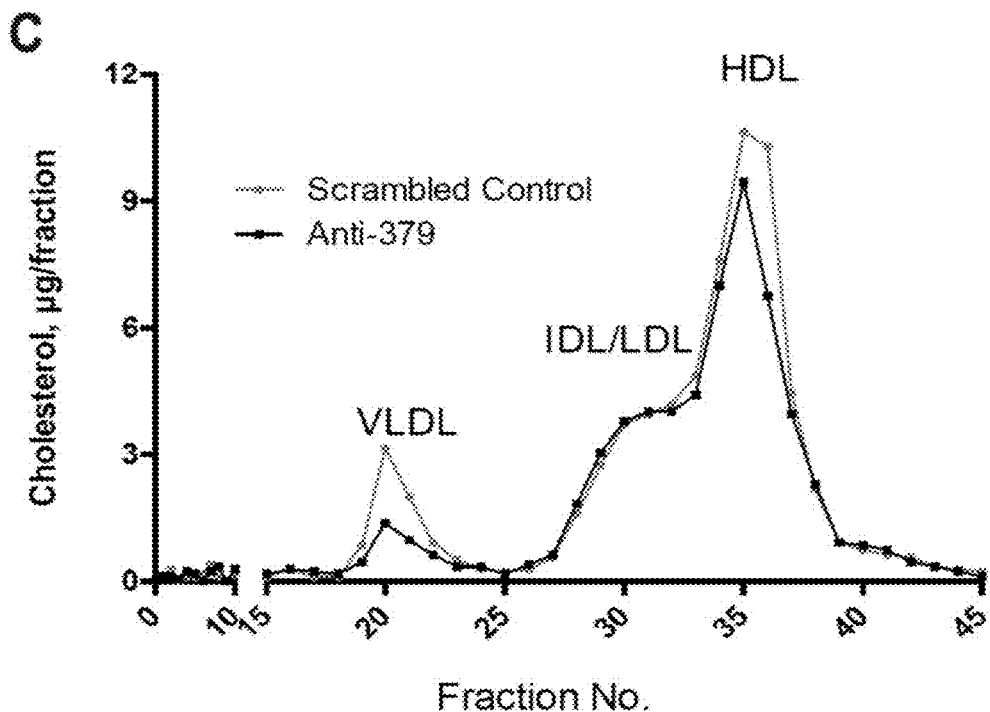
Figure 8D:
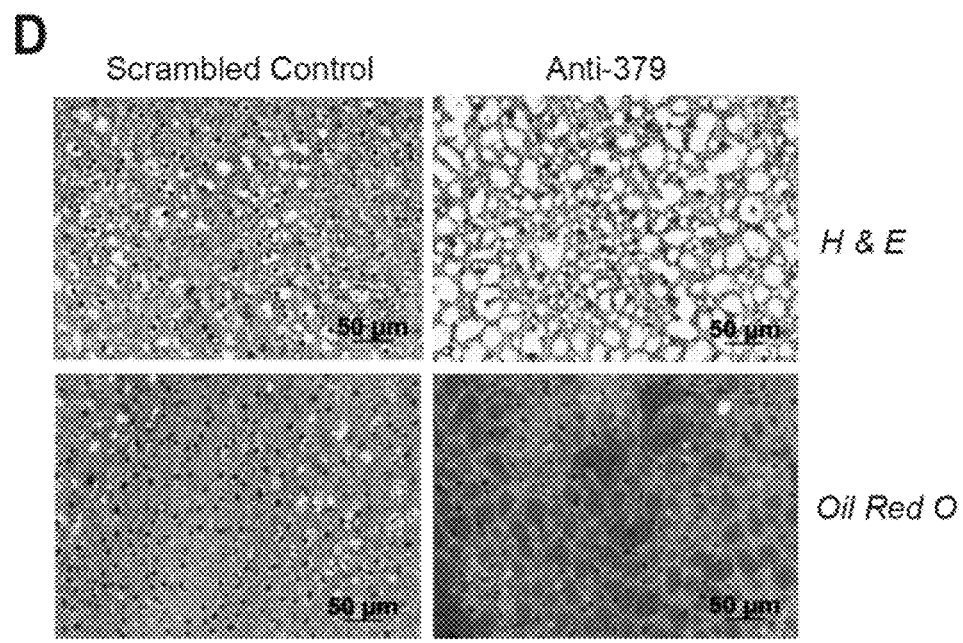

To this end, the inventors silenced hepatic expression of miRNA379 by LNA delivery into 12 weeks old db/db mice with fully established hyperglucocorticoidemia, hyperlipidemia, and hyperglycemia. 7 days after LNA delivery, hepatic miRNA379 deficiency led to a marked reduction in serum VLDL-TG and improved blood glucose levels along with an ameliorated insulin resistance index (FIG. 4A, 8A, 4B, 4C). In line with results from wild-type animals, miRNA379 LNA treatment had no major effect on circulating cholesterol levels (FIG. 8B, 8C), again verifying the specificity of the observed effects for the TG arm of systemic lipid homeostasis. Indeed, in congruence with the ApoB TG clearance properties of hepatic LSR and LDLR, miRNA379 deficiency promoted retention of TG in the liver (FIG. 8D), and caused a significant induction of both LSR and LDLR protein expression as compared with control LNA-treated animals (FIG. 4D).

Figure 4E:
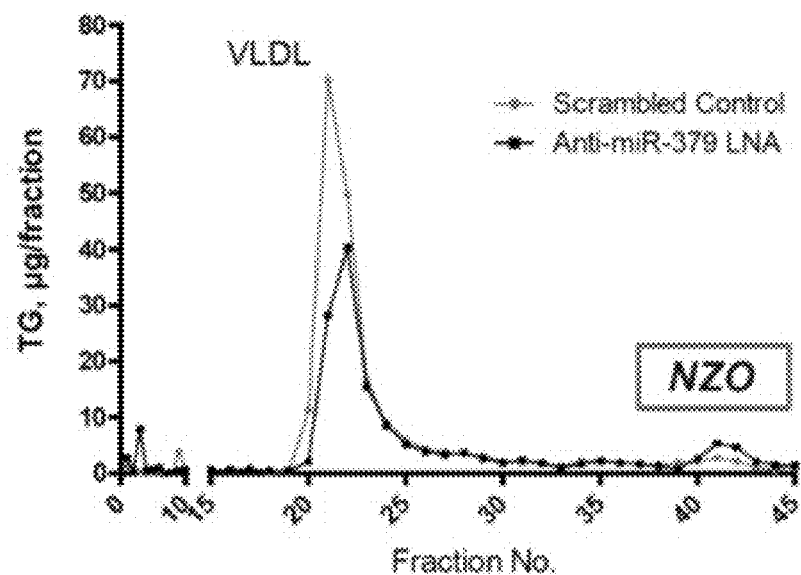
Figure 4F:
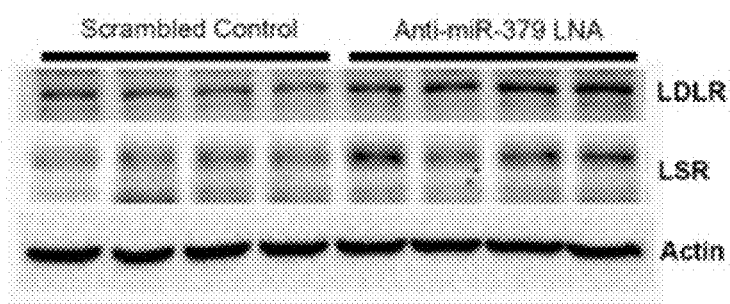

To corroborate these findings in an independent multigenic obesity model, we treated New Zealand Obese (NZO) mice with miR-379-specific or control LNA. In line with the results from the db/db studies, silencing of hepatic miR-379 significantly reduced serum VLDL-TG levels with a minor impact on serum cholesterol (FIG. 4E) and elevated hepatic protein expression of both LDLR and LSR (FIG. 4F).

Figure 4G:
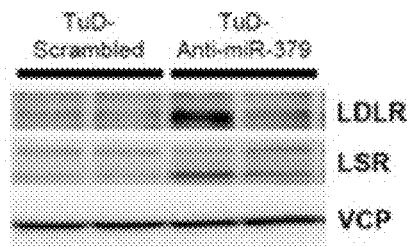
Figure 4H:
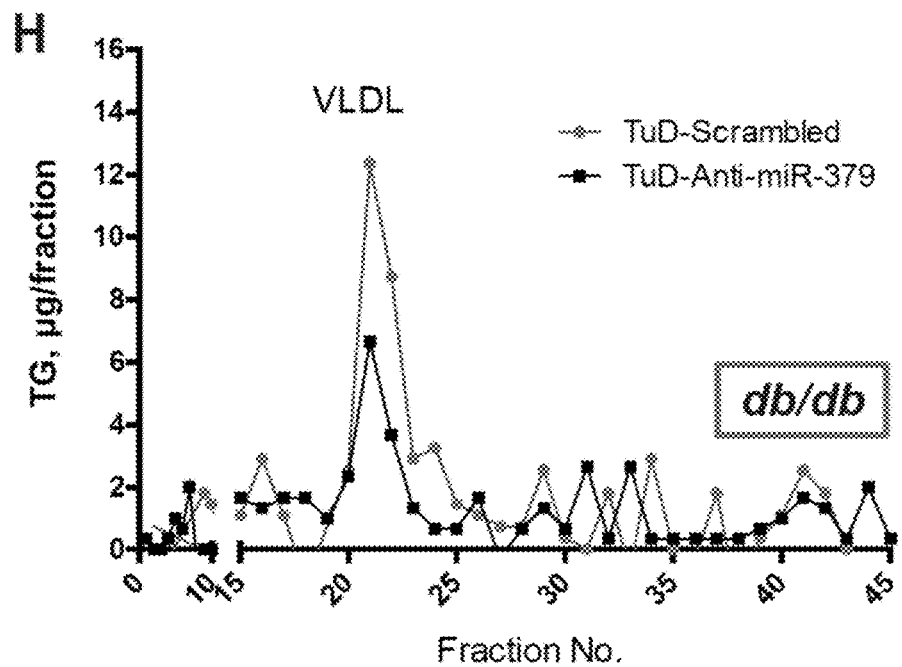
Figure 4I:
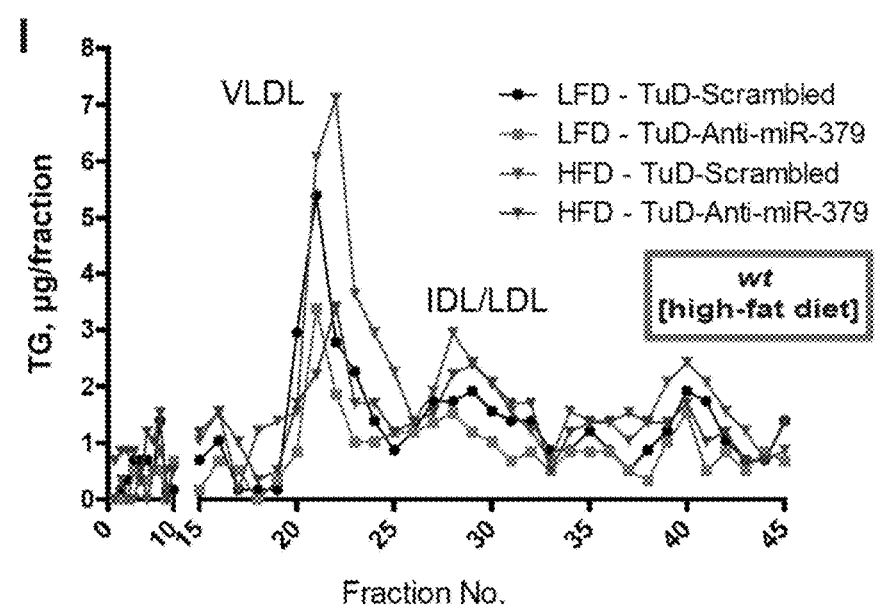
Figure 5A:
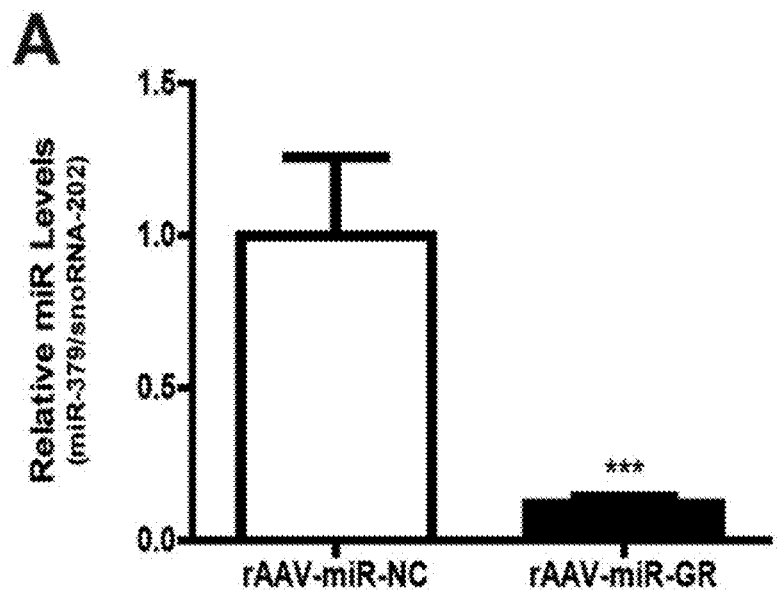
Figure 5B:
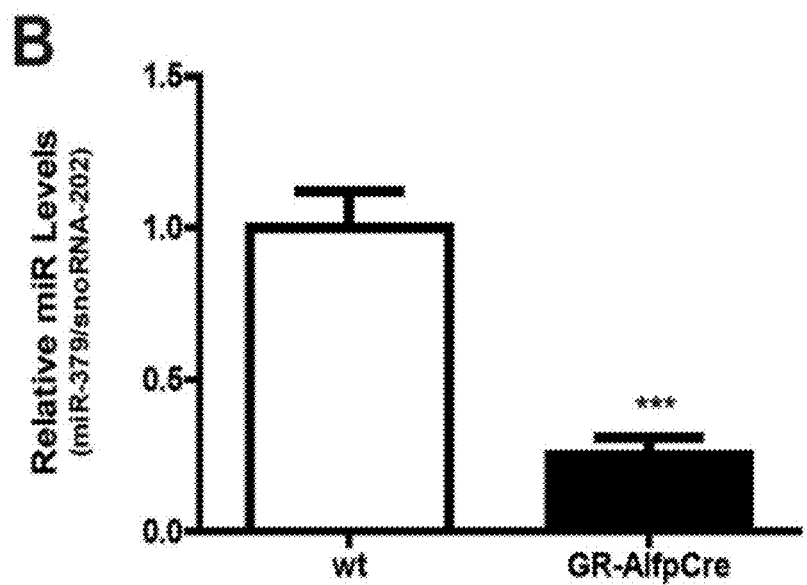

To validate our findings by an independent experimental system, we designed and employed a novel miR-379-specific tough decoy (TuD-Anti-miR-379) approach in db/db animals. Hepatic AAV-mediated delivery of TuD-Anti-miR-379 under control of a hepatocyte specific promoter induced LSR and LDLR protein expression in liver (FIG. 4G) and substantially decreased serum VLDL-TG levels in 14 week old db/db mice (FIG. 4H), while only weakly impairing serum cholesterol levels (not shown). Importantly, TuD-Anti-miR-379 delivery into wild-type animals fed a high fat diet for 12 weeks also lowered circulating VLDL-TG and—albeit less pronounced—cholesterol levels as demonstrated by FPLC (FIG. 4I), indicating that miR-379 also controls systemic TG homeostasis under conditions of dietary energy excess.

Figure 9A:
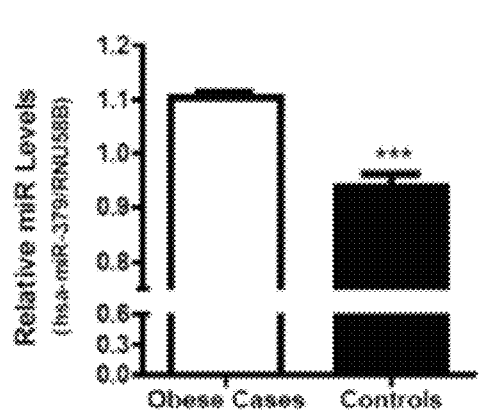
FIGS. 9A-9E: miR-379 levels correlate with serum cortisol and triglyceride levels in humans. (9A) Hepatic miR-379 levels in obese patients (n=64) and healthy controls (n=10). (9B-9C) Serum triglyceride (9B) and cortisol (9C) levels in obese and healthy control individuals. Bar graphs show mean±SEM; t-test: *$p<0.001$, $p<0.01$, or *$p<0.05$. (9D-9E) Correlation analyses of human hepatic miR-379 and serum cortisol (9D) or triglycerides (9E) (n=74). Shown are the Spearman's Rank coefficients and p-values. Sample population was stratified into diabetic-obese, nondiabetic obese, and controls based on statistically significant interaction effects of the groups and serum parameters in a multiple linear regression model.
Figure 9B:
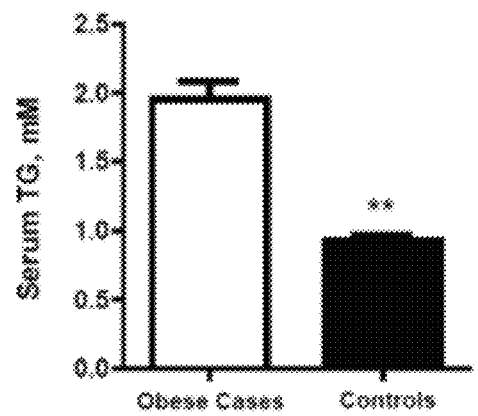
Figure 9C:
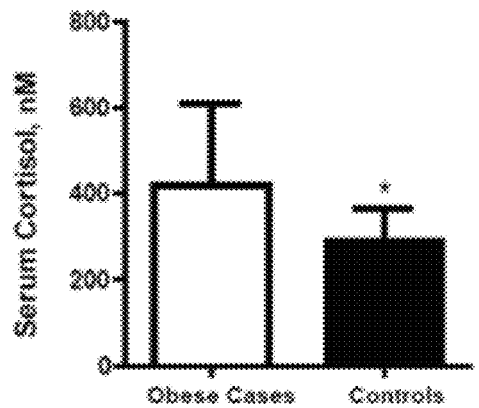
Figure 9D:
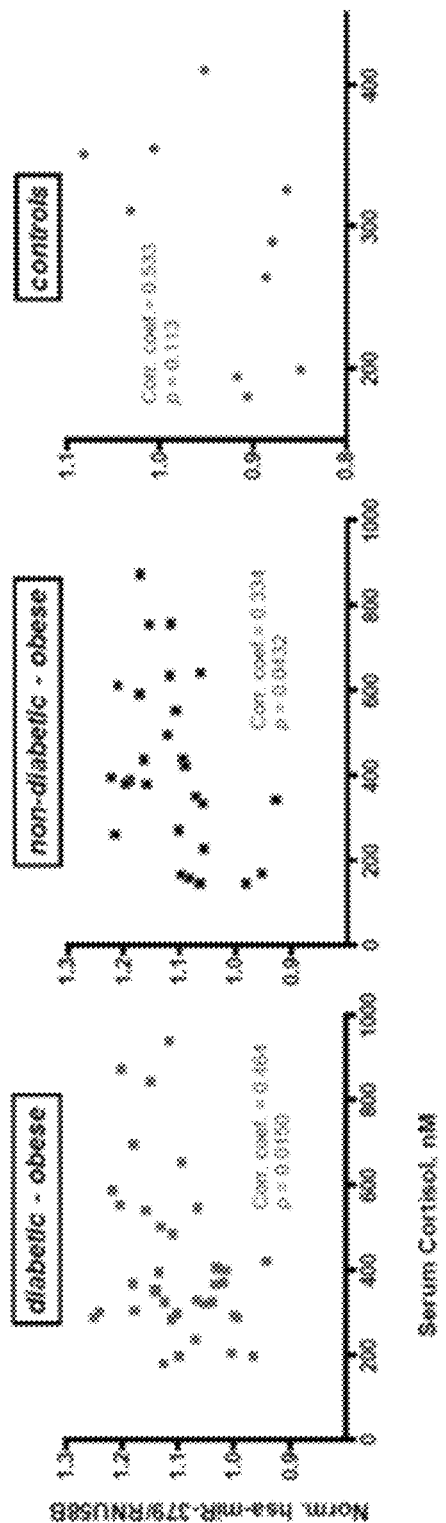
Figure 9E:
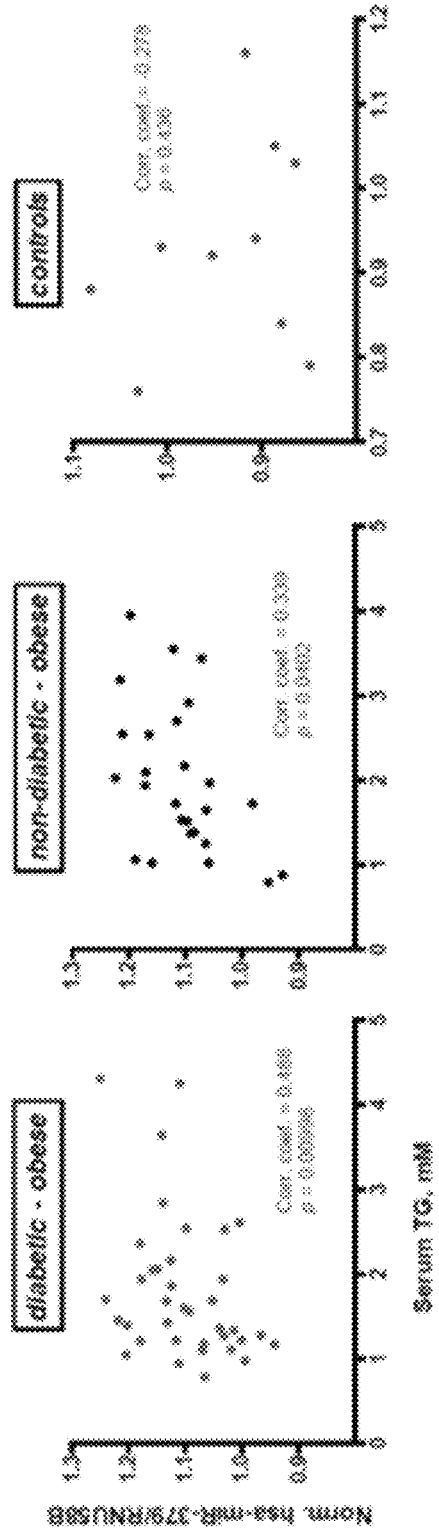

Example 5: Hepatic miR-379 Levels Correlate with Serum Cortisol and TG in Human Obese Patients Together, these studies demonstrate that the GC/GR-inducible miR-379 pathway represents a critical checkpoint in systemic dyslipidemia in diabesity, and that selective targeting of miR-379 in the liver can be used as a therapeutic measure against GC-dependent hypertriglyceridemia. To finally test the validity of this assumption in humans, we investigated hepatic miR-379 expression in a clinically well-defined cohort of more than 70 individuals. In line with our experimental findings in animals, hepatic miR-379 levels were lower in lean individuals as compared with obese subjects (FIG. 9A), and positively correlated with serum cortisol and TG levels in this patient cohort as well as in the obese-only sub-cohorts, respectively (FIG. 9B-E), indicating that the GC/GR-dependent control of the miR-379 pathway represents a conserved (patho) physiological mechanism in obesity-dependent lipid homeostasis.

Materials and Methods

Recombinant Viruses

For long-term inactivation of GR, adeno-associated viruses (AAV) encoding GR-specific miRNA were established as described previously (Rose A J et al., 2011). Recombinant viruses were produced in 293T cells through triple co-transfection of the recombinant viral backbone vector with the helper plasmids. Viruses were purified using the iodoxanol method, dialyzed, and titrated by RT-qPCR.

For liver-specific overexpression of miR-379, the same recombinant viral backbone vector was used as above. Mir-379 genomic sequence±100 bp was PCR amplified with primers harboring BglII and SalI restriction sites. PCR product was then digested with the appropriate restriction enzymes and cloned into pcDNA6.2-GW/EmGFP-miR ("BLOCK-iT™ PolI miR RNAi Expression Vector Kit" (Invitrogen, Darmstadt, DEU)). The construct was then tested in Hepa1-6 cell line and primary hepatocytes together with the corresponding control prior to subcloning into the AAV vector.

Adenoviruses expressing Lsr-specific or non-specific control oligonucleotides were cloned as described previously (Herzig S et al., 2003; Narvekar P et al., 2009). Viruses were purified using the CsCl method and dialyzed against phosphate-buffered saline containing 10% glycerol prior to animal injection.

Design and Synthesis of LNA Oligonucleotides

The LNA oligonucleotides were synthesized as unconjugated and fully phosphorothioated oligonucleotides (Exiqon A/S, Vedbaek, Denmark). The perfectly matching, 15-mer LNA-antimiR oligonucleotide (5'-GTTCCATAGTCTACC-3'; SEQ ID NO: 13) was complementary to nucleotides 2-16 in the mature miR-379 sequence. The scrambled control LNA oligonucleotide was synthesized with the following sequence: 5'-ACGTCTATACGCCCA-3' (SEQ ID NO: 14).

Animal Experiments

Male, 8- to 12-week-old C57BL/6J, db/db, New Zealand black (NZB), and New Zealand obese (NZO) were obtained from Charles River Laboratories (Brussels, Belgium).

$GR^{dim/dim}$, $GR^{AlfpCre}$, and corresponding wild-type littermates were obtained and bred as previously described (Rose A J et al., 2011). All mice were maintained on a 12 h light-dark cycle with regular unrestricted diet and had free access to drinking water. In all cases, mice were acclimated to the housing facility and control diet food (% E: 70 carbohydrate, 20 protein, 10 fat; New Brunswick, USA) for at least one week prior to experimentation. For starvation experiments, animals were fasted for 24 h with free access to water or fasted and refed for the remaining 6 h.

To examine the effects of long-term liver GR knockdown on the expression of microRNAs, mice were administered with $5 \times 10^{11}$ viral genomes of non-specific negative control or GR-specific miRNA bearing adeno-associated virus. Mice were kept on normal diet for 6 weeks after which fasted overnight for 14-16 h and then euthanized.

To examine the effects of glucocorticoids on hepatic microRNA levels, 7-8 wk old male, CS7L/J mice were with 9α-Fluoro-16α-methylprednisolone (Dexamethasone, Dex; 1 mg/kg, Sigma-Aldrich, Munich, Germany) or Vehicle (Veh, 2% ethanol in isotonic saline) for 14 d after which they were sacrificed between ZT1-4 in the random fed state.

To examine the importance of GR dimerisation and DNA binding activity, 7-10 wk old male homozygous glucocorticoid receptor dimerisation deficient ($GR^{dim/dim}$) (Reichardt H M et al., 1998) and wild-type littermate mice were treated daily with 9α-Fluoro-16α-methylprednisolone (dexamethasone, Dex; 1 mg/kg, Sigma-Aldrich, Munich, Germany) or Vehicle (Veh, 2% ethanol in isotonic saline) for 14 d after which they were sacrificed in the overnight fasted state.

To examine the effects of genetic hepatocyte-specific knockout of GR in mice, liver samples from $GR^{AlfpCre}$ (Opherk C et al., 2004) and wild-type littermate mice were taken in the fasted state as previously reported (Lemke U et al., 2008).

To investigate the metabolic effects of the loss of miR-379 in the liver, C57BL/6J and db/db mice were injected with 15 mg/kg BW of anti-379 specific LNA or scrambled control (both reconstituted in water and diluted with isotonic saline) for two consecutive days. Mice were then euthanized 7 d or 14 d post-injection in the random fed state.

To evaluate if the metabolic effects of miR-379 inhibition are still observable upon knockdown of the Lsr target, C57BL/6J mice were injected with adenoviruses, Lsr-specific or non-specific, as described previously (Narvekar P et al., 2009). Three days after virus injection, mice were injected with anti-379 specific LNA or scrambled control as indicated above. Mice were then euthanized after 7 d post-LNA injection.

Organs including liver, epididymal fat pads, and gastrocnemius muscles were collected after the corresponding time periods, weighed, snap-frozen, and used for further analysis. Whole blood was also collected for serum isolation which was then kept at −80° C. until needed for analyses. Total body fat content was determined by an Echo MRI body composition analyzer (Echo Medical Systems, Houston, Tex., USA). Animal handling and experimentation was done in accordance with National Institutes of Health (NIH) guidelines and approved by local authorities.

Tissue and Serological Metabolite & Hormone Analyses

To ensure an analysis representative of the whole liver, frozen liver samples were pulverized (Bessman Tissue Pulveriser, 189-476, VWR International GmbH, Darmstadt, DEU) and subsequent tissue powder aliquots were weighed and prepared for analyte extractions. Hepatic lipids were extracted as described previously (Herzig S et al., 2003).

Serum levels of glucose were measured using an automated analyser (One Touch, Lifescan, Neckargemünd, Germany). Commercially available kits were used to quantify serum, triglycerides (Sigma-Aldrich, Munich, Germany), cholesterol (RANDOX, Crumlin, NIR), non-esterified fatty acids (WAKO, Neuss, Germany), ketone bodies (WAKO, Neuss, Germany), alanine amino transferase (Fischer Scientific, Schwerte, Germany), corticosterone (Assay Designs, Ann Arbor, USA), and insulin (Mercodia, Uppsala, Sweden). Liver triglycerides, cholesterol, free fatty acids, & ketone bodies were analyzed from the extracts using the same commercial kits as in serum and. Values were calculated as millimolar concentration per liter (serum) or per gram wet tissue (liver).

Fast Protein Liquid Chromatography

Serum from specified number of mice per experimental group was pooled and subjected to fast protein liquid chromatography as previously described (Lichtenstein L et al., 2007). Cholesterol and TG were measured in the eluted fractions using commercial kits as above. Values were calculated as µg of triglyceride or cholesterol per fraction.

Hepatic VLDL Release

VLDL production was determined after tyloxapol (Sigma, Munich, Germany) injection as described (Mandard et al., 2006). Briefly, seven C57BL/6J mice per group were fasted overnight for 16 hours. On the following day, 404 of blood was drawn from each mouse by cutting the tip of the tail. The volume of tyloxapol in µL required per mouse was approx. 3 times that of the weight of the mouse in grams; i.e. a 25 g mouse required 75 µL of a 20% solution. Specified amounts were administered via the tail vein and 40 µL blood samples were taken every 50 min for 2.5 hours. The mice were eventually sacrificed at 300 minutes. The serum TG values were determined (see above) and plotted vs. time.

VLDL Clearance

Human VLDL was isolated from fasted serum samples by ultracentrifugation as described (Redgrave T G et al., 1975). Briefly, 3.5 ml serum was put in a polyallomer tube SW40Ti and mixed with 1.39 g KBr, overlayered with 332.8 ml of a NaCl/KBr solution (D=1.063, 1.019, and 1.006 g/ml) and run for 18 hr at 40,000 rpm. Human VLDL (20 mg) was injected into each animal, and serum samples were taken at 2, 10, 30, 60, and 120 min. Serum human ApoB-100 levels were measured using a human-specific ApoB ELISA. For the ELISA, the inventors used a primary coating antibody generated against human apoB-100 (mAb47, kindly supplied by J. Witztum, University of San Diego, USA), in a concentration of 2 mg/well IgG protein in TBS/EDTA/BHT and a secondary biotinylated polyclonal antibody raised in goat against human ApoB in a concentration of 4 ug/well in 1.5% BSA/TBS/0.1% Tween. To prevent nonspecific binding, plates were blocked with 1.5% BSA/TBS/0.1% Tween. Samples were diluted 1:25. Absorbance was read 30 min after addition of TMB and termination of the reaction with 2 M $H_2SO_4$ at 450 nm (Groot P H et al., 1991).

LPL Activity

LPL activity measurements were performed as described (Klingenspor M et al., 1989) using frozen adipose tissue samples.

RNA Isolation and Quantitative Taqman RT-PCR

Total RNA was extracted from homogenized mouse liver or cell lysates using Qiazol reagent and miRNeasy® Mini Kit (Qiagen, Hilden, Germany). cDNA was prepared by reverse transcription using the M-MuLV enzyme and Oligo dT primer (Fermentas, St. Leon-Rot, Germany). cDNAs were amplified using assay-on-demand kits and an ABI-PRISM 7700 Sequence detector (Applied Biosystems, Darmstadt, Germany). RNA expression data were normalized to levels of TATA-box binding protein (TBP) RNA. For microRNA RT-PCR, Applied Biosystems' TaqMan® MicroRNA Reverse Transcription Kit (Life Technologies GmbH, Darmstadt, Germany) was used together with TaqMan® MicroRNA Assay Primer. snoRNA-202 was used as internal control for miRNA quantifications. Particular product numbers for probe sets can be provided upon request.

Protein Analysis

Protein was extracted from frozen organ samples, cultured cell lines or primary cells in cell lysis buffer (Rose A J et al, 2007) and 10 mg of protein were loaded onto 5-12% SDS-polyacrylamide gels and blotted onto nitrocellulose membranes. Western blot assays were performed as described (Herzig S et al, 2001) using antibodies specific for glucocorticoid receptor (Santa Cruz Biotech., Heidelberg, Germany), LSR (DKFZ, Heidelberg, Germany), LDLR (Abcam, Cambridge, UK), APOB (Santa Cruz Antibodies) Actin (Sigma, Munich, Germany) or VCP (Abcam). Band optical densities were quantified using ImageJ software (NIH).

Histological Examinations

For hematoxylin and eosin (H&E) and oil red O lipid staining, 5 mm cryosections of liver embedded in Tissue Tek OCT compound (Sakura, Netherlands) were fixed in Baker's formol. Nuclei were counterstained with hematoxylin.

Cell Culture and Transfections

Cells were cultured with 10% FBS in DMEM (HEK293, Hepa1-6) supplemented with glutamine in the presence or absence of antibiotics depending on the mode of transfection application. Plasmid constructs, microRNA mimics (Fisher Scientific, Schwerte, Germany), and LNAs (Exiqon A/S, Vedbaek, Denmark) were transfected into cells using PEI (Polysciences Europe GmBbH, Eppelheim, Germany), promofectin (for primary hepatocytes) (Promocell GmBH, Heidelberg, Germany), lipofectamine 2000 (Invitrogen, Karlsruhe, Germany), or $CaCl_2$ method according to the manufacturer's or using the standard protocol. Plasmid constructs were transfected from 50-2000 ng amounts while miRNA mimics and LNAs were transfected from 50-100 nM concentrations. In all cell culture studies, cells were transfected at 50% confluency. The effect of overexpression/knockdown constructs, mimics, or LNAs were evaluated 24-48 hrs post-transfection.

Primary mouse hepatocytes were isolated and cultured as described (Klingmuller J et al., 2006). Briefly, male 8-12 week old C57BL/6J were anesthetized and after opening the abdominal cavity, the liver was perfused at 37° C. with Hanks buffer I and II. The liver capsule was removed and carefully dissected in Williams' medium E adhesion (WMEa; supplemented with 10% FCS; 1.5 µM Insulin; 100 nM Dexamethasone; 2 mM L-glutamine and 1% Penicillin/Streptomycin). The cell suspension was filtered and washed twice with WMEa at room temperature. Cells were centrifuged and the pellet was resuspended in WMEa. Primary hepatocytes were seeded on collagen I-coated 6-well plates at a density of $1*10^6$ living cells/well in WMEa. After 4 h incubation, non-attached cells were removed by washing once and replacing WMEa with WME (supplemented with 10% FCS; 2 mM L-glutamine and 1% Penicillin/Streptomycin). A more severe washing to remove dead cells was performed after subsequent 16-18 h of cells in culture and then the cells were treated accordingly.

Seahorse β-Oxidation Metabolic Flux Assay

Mitochondrial β-oxidation activity was determined using an XF96 Extracellular Flux Analyser (Seahorse, Copenhagen). Prior to the experiment, 1000 Hepa1-6 cells were seeded per well in a 96-well format and transfected with miR-379 overexpression and knockdown constructs using Lipofectamine 2000 (Invitrogen, Karlsruhe, Germany). The assay was performed according to the manufacturer's protocol and using 200 µM BSA-Palmitate conjugate, 0.5 mM carnitine (Sigma-Aldrich, Munich, Germany), and 100 µM etomoxir (Sigma-Aldrich, Munich, Germany). Oxygen consumption rate was calculated and normalized to protein content, as determined by Sulforhodamine B staining.

Microarray Expression Profiling

MicroRNA profiling was performed on hepatic total RNA extracts from [1] wild type and db/db mice and from [2] control mice and rAAV-treated mice for liver-specific GR-knockdown. RNA isolation, cDNA and cRNA synthesis, and hybridization to arrays of type GeneChip® miRNA 2.0 Array (Affymetrix, Freiburg, Germany) was performed according to the manufacturer's recommendations. Four arrays per group were hybridized. Microarray data were analyzed based on ANOVA using a commercial software package (Micro Array Solution, version 1.0; SAS Institute, Cary, N.C.). Standard settings were used, except for the following specifications: log-linear mixed models were fitted for values of perfect matches, with genotype considered to be constant and the array identification, random. Custom CDF with Unigene-based gene/transcript definitions was used to annotate the arrays. Affected biological pathways reflected by the differential gene expression were determined by ORA based on Fisher's exact test.

Northern Blotting

For detection of miRNA expression, northern blotting was performed as described previously (Varallyay E et al., 2008). Briefly, 20-40 µg of total RNA was separated on 15% TBE-Urea polyacrylamide gels and semi-dry transferred to Hybond $N^+$ membrane (Amersham, GE Healthcare, Germany). Complete LNA probe complementary to miR-379, miR-122, & let-7a were designed as described in the microRNA registry (see Worldwide Website: sanger.ac.uk/). 20 pmol of the probe was labelled with T4 polynucleotide kinase (New England Biolabs) and 20 µCi of $[\gamma^{-32}P]$ ATP (250 µCi; Perkin Elmer Inc., Rodgau, Germany). Hybridizations were performed at 50° C. for 16 h in a 100 mL of the small RNA hybridization buffer (Formamide·1M NaCl·0.2M Na-phosphate·0.04M EDTA·Denhardt's solution·SDS). The membrane was washed several times and exposed to an erased phosphor screen which was then scanned & analyzed after at least 4 hours. For stripping and re-probing, the membrane was incubated at RT with boiling stripping solution (0.02×SSC·0.01% SDS) and hybridized with another probe after 30 minutes of prehybridization. U6RNA probe (5'-CACGAATTTGCGTGTCATCCTT-3') was used as loading control.

Ex Vivo Human Liver Samples

To examine the effects of glucocorticoid treatment or excess to human hepatic microRNAs, a healthy piece of freshly resected liver from an individual (Age: 51y, Sex: female) undergoing liver surgery to remove a tumor was utilized. From this sample, small pieces (10-20 mg) were carefully dissected and incubated (37° C., 5% CO2) in quadruplicate in non-adhesive tissue culture plates (Greiner Bio-One, Frickenhausen, Germany) in Williams' medium E (+2 mM L-Glutamine and 0.1% BSA; Biochrom AG, Berlin, Germany) containing 0.11% EtOH (Vehicle), 104 RU486 (Sigma-Aldrich, Munich, Germany), 0.104 dexamethasone (Sigma-Aldrich, Munich, Germany) and 1 µM RU486+0.1 µM dexamethasone. Samples were incubated for 30 min prior to treatment with or without RU486. Incubations were ceased at 3 h after treatment upon which the tissue pieces were washed with PBS, rapidly frozen in liquid nitrogen and stored at −80° C. until needed. Each volunteer gave written informed consent before participation, and the study was approved by the local ethics committee.

Human Liver Samples

Subjects. miR-379 expression was investigated in liver tissue samples obtained from 10 Caucasian healthy donors and 64 Caucasian obese men and women with (n=27) or without (n=37) type 2 diabetes who underwent open abdominal surgery for Roux-en-Y bypass, sleeve gastrectomy or elective cholecystectomy. A small liver biopsy was taken during the surgery, immediately frozen in liquid nitrogen and stored at −80° C. until further preparations. The phenotypic characterization of the cohort has been performed as described previously. All baseline blood samples were collected between 8 and 10 am after an overnight fast. All study protocols have been approved by the Ethics committee of the University of Leipzig (363-10-3013122010 and 017-12-230112). All participants gave written informed consent before taking part in the study.

hsa-miR-379 Studies: Human miR-379 mRNA expression was measured by quantitative realtime RT-PCR in a fluorescent temperature cycler using the TaqMan assay, and fluorescence was detected on an ABI PRISM 7000 sequence detector (Applied Biosystems, Darmstadt, Germany). Total RNA was isolated as described above. Applied Biosystems' TaqMan® MiRNA Reverse Transcription Kit (Life Technologies GmbH, Darmstadt, Germany) was used together with TaqMan® MiRNA Assay Primer for hsa-miR-379 to quantify the miRNA level. RNU58B was used as internal control for miRNA quantifications.

Bioinformatics and miRNA Target Site Analysis

UCSC Genome Browser (see Worldwide Website: genome.ucsc.edu/index.html) was utilized to identify putative promoter region of the microRNA and scan the region for results of experiments from transcription factor ChIP-Seq (Meyer L R et al., 2012). For microRNA target prediction, miR-Walk (see Worldwide Website: umm.uni-heidelberg.de/apps/zmf/mirwalk/) and RNA22 (see Worldwide Website: cm.jefferson.edu/rna22v1.0/) (Dweep H et al., 2011; Miranda K C et al., 2006) were utilized.

Statistical Analyses

For each experiment, means and SEM of parameters measured were determined. Statistical analyses were performed using student's t-test in one-factorial designs. Correlation was determined using Pearson's correlation coefficient; F-test was applied to determine significance. For multifactorial study designs, two-way ANOVA were used when appropriate. Holm-Sidak post hoc was applied when significant differences were found with an overall significance level=0.05. All analyses were carried out with SigmaPlot v.12 software (Systat Software GmbH, Erkrath Germany).

REFERENCES

Benetatos, L., Hatzimichael, E., Londin, E., Vartholomatos, G., Loher, P., Rigoutsos, I., and Briasoulis, E. (2013). The microRNAs within the DLK1-DIO3 genomic region: involvement in disease pathogenesis. Cell Mol Life Sci 70, 795-814.

Chahil, T. J., and Ginsberg, H. N. (2006). Diabetic dyslipidemia. Endocrinol Metab Clin North Am 35, 491-510, vii-viii.

Gebhard, C., Huard, G., Kritikou, E. A., and Tardif, J. C. (2013). Apolipoprotein B antisense inhibition—update on mipomersen. Curr Pharm Des 19, 3132-3142.

Kersten, S., Seydoux, J., Peters, J. M., Gonzalez, F. J., Desvergne, B., and Wahli, W. (1999). Peroxisome proliferator-activated receptor alpha mediates the adaptive response to fasting. J Clin Invest 103, 1489-1498.

Kulozik, P., Jones, A., Mattijssen, F., Rose, A. J., Reimann, A., Strzoda, D., Kleinsorg, S., Raupp, C., Kleinschmidt, J., Muller-Decker, K., Wahli, W., Sticht, C., Gretz, N., von Loeffelholz, C., Stockmann, M., Pfeiffer, A., Stohr, S., Dallinga-Thie, G. M., Nawroth, P. P., Berriel Diaz, M., and Herzig, S. (2011). Hepatic deficiency in transcriptional cofactor TBL1 promotes liver steatosis and hypertriglyceridemia. Cell Metab 13, 389-400.

Leiter, E. H., and Reifsnyder, P. C. (2004). Differential levels of diabetogenic stress in two new mouse models of obesity and type 2 diabetes. Diabetes 53 Suppl 1, S4-11.

Lemke, U., Krones-Herzig, A., Diaz, M. B., Narvekar, P., Ziegler, A., Vegiopoulos, A., Cato, A. C., Bohl, S., Klingmuller, U., Screaton, R. A., Muller-Decker, K., Kersten, S., and Herzig, S. (2008). The glucocorticoid receptor controls hepatic dyslipidemia through Hes1. Cell Metab 8, 212-223.

Luk, J. M., Burchard, J., Zhang, C., Liu, A. M., Wong, K. F., Shek, F. H., Lee, N. P., Fan, S. T., Poon, R. T., Ivanovska, I., Philippar, U., Cleary, M. A., Buser, C. A., Shaw, P. M., Lee, C. N., Tenen, D. G., Dai, H., and Mao, M. (2011). DLK1-DIO3 genomic imprinted microRNA cluster at 14q32.2 defines a stemlike subtype of hepatocellular carcinoma associated with poor survival. J Biol Chem 286, 30706-30713.

Mandard, S., Zandbergen, F., van Straten, E., Wahli, W., Kuipers, F., Muller, M., and Kersten, S. (2006). The fasting-induced adipose factor/angiopoietin-like protein 4 is physically associated with lipoproteins and governs plasma lipid levels and adiposity. J Biol Chem 281, 934-944.

Narvekar, P., Berriel Diaz, M., Krones-Herzig, A., Hardeland, U., Strzoda, D., Stohr, S., Frohme, M., and Herzig, S. (2009). Liver-specific loss of lipolysis-stimulated lipoprotein receptor triggers systemic hyperlipidemia in mice. Diabetes 58, 1040-1049.

Opherk, C., Tronche, F., Kellendonk, C., Kohlmuller, D., Schulze, A., Schmid, W., and Schutz, G. (2004). Inactivation of the glucocorticoid receptor in hepatocytes leads to fasting hypoglycemia and ameliorates hyperglycemia in streptozotocin-induced diabetes mellitus. Mol Endocrinol 18, 1346-1353.

Reynolds, R. M., Walker, B. R., Syddall, H. E., Andrew, R., Wood, P. J., Whorwood, C. B., and Phillips, D. I. (2001). Altered control of cortisol secretion in adult men with low birth weight and cardiovascular risk factors. J Clin Endocrinol Metab 86, 245-250.

Rose, A. J., Diaz, M. B., Reimann, A., Klement, J., Walcher, T., Krones-Herzig, A., Strobel, O., Werner, J., Peters, A., Kleyman, A., Tuckermann, J. P., Vegiopoulos, A., and Herzig, S. (2011). Molecular control of systemic bile acid homeostasis by the liver glucocorticoid receptor. Cell Metab 14, 123-130.

Rose, A. J., Vegiopoulos, A., and Herzig, S. (2010). Role of glucocorticoids and the glucocorticoid receptor in metabolism: insights from genetic manipulations. J Steroid Biochem Mol Biol 122, 10-20.

Rosenson, R. S., and Underberg, J. A. (2013). Systematic Review: Evaluating the Effect of Lipid-Lowering Therapy on Lipoprotein and Lipid Values. Cardiovasc Drugs Ther.

Rottiers, V., and Naar, A. M. (2012). MicroRNAs in metabolism and metabolic disorders. Nat Rev Mol Cell Biol 13, 239-250.

Stenvang, J., Petri, A., Lindow, M., Obad, S., and Kauppinen, S. (2012). Inhibition of microRNA function by antimiR oligonucleotides. Silence 3, 1.

The invention claimed is:

1. A method for the treatment or prevention of a glucocorticoid hormone driven metabolic dysfunction and/or a disease associated with elevated serum levels of triglycerides, wherein said method comprises administering, to a patient in need of such treatment, an inhibitor of a micro RNA (miR), or of a target site of a miR, wherein the miR is miR-379.

2. The method according to claim 1, wherein the inhibitor is a nucleic acid molecule comprising a sequence complementary to, or hybridizing under stringent conditions to, the sequence of said miR, or said target site of said miR.

3. The method according to claim 1, wherein the inhibitor comprises a chemical modification selected from phosphorothioate DNA (PS), 2'-O-methyl RNA (OMe), 2'-O-methoxy-ethyl RNA (MOE), peptide nucleic acid (PNA), N3'-P5' phosphoroamidate (NP), 2'-fluoro-arabino nucleic acid (FANA), locked nucleic acid (LNA), morpholino phosphoroamidate (MF), cyclohexene nucleic acid (CeNA), and tricycle-DNA (tc-DNA).

4. The method, according to claim 1, wherein the inhibitor comprises a sequence according to SEQ ID NO: 13 (GTTC-CATAGTCTACC).

5. A method for altering glucocorticoid activity in a human liver or fat cell, the method comprising the steps of:
   a) for decreasing glucocorticoid activity in said cell,
   b) for increasing glucocorticoid activity in said cell.

6. The method according to claim 5, where the activity of a miR is inhibited by introducing into said cell an antisense molecule (antimiR) targeting said miR or a blockmiR targeting the target site of said miR; and/or wherein the activity or expression of said miR is increased by introducing into said cell an expression construct comprising an expressible sequence of said miR.

7. The method according to claim 5, which is an ex-vivo or in-vitro method.

8. The method, according to claim 1, used to treat obesity, diabetes, diabesity, metabolic syndrome, insulin resistance, hyperglycemia, systemic dyslipidemia, Cushing's syndrome, adverse effects associated with glucocorticoid treatment or excess, atherosclerosis, heart disease, stroke or growth defects.

9. A method for the treatment or prevention of a glucocorticoid hormone driven metabolic dysfunction and/or a disease associated with elevated serum levels of triglycerides, wherein said method comprises administering, to a patient in need of such treatment, an inhibitor of a micro RNA (miR), or of a target site of a miR, wherein said miR is miR-379.

\* \* \* \* \*

UNITED STATES PATENT AND TRADEMARK OFFICE
CERTIFICATE OF CORRECTION

PATENT NO. : 10,041,070 B2
APPLICATION NO. : 15/033442
DATED : August 7, 2018
INVENTOR(S) : Mauricio Berriel Diaz et al.

Page 1 of 1

It is certified that error appears in the above-identified patent and that said Letters Patent is hereby corrected as shown below:

In the Specification

Column 12,
Line 53, "group). (E)" should read -- group). (2E) --.

Column 20,
Line 26, "404 of blood" should read -- 40μL of blood --.

Column 22,
Line 58, "(Vehicle), 104 RU 486" should read -- (Vehicle), 1μM RU486 --.
Line 59, "0.104 dexamethasone" should read -- 0.1μM dexamethasone --.

In the Claims

Column 29,
Lines 6-7, "activity in said cell, b) for increasing glucocorticoid activity in said cell." should read -- activity in said cell, inhibiting the activity or expression of miR-379 or b) for increasing glucocorticoid activity in said cell increasing the activity or expression of miR-379. --.

Signed and Sealed this
Thirtieth Day of April, 2019

Andrei Iancu
*Director of the United States Patent and Trademark Office*